(12) United States Patent
Ai et al.

(10) Patent No.: US 8,697,031 B2
(45) Date of Patent: Apr. 15, 2014

(54) DUAL FUNCTION POLYMER MICELLES

(75) Inventors: Hua Ai, Sichuan (CN); Jeffrey L. Duerk, Avon Lake, OH (US); Chris Flask, Avon Lake, OH (US); Jinming Gao, Plano, TX (US); Jonathan S. Lewin, Baltimore, MD (US); Xintao Shuai, Cleveland Heights, OH (US); Brent Weinberg, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1656 days.

(21) Appl. No.: 11/569,989

(22) PCT Filed: Jun. 2, 2005

(86) PCT No.: PCT/US2005/019308
§ 371 (c)(1),
(2), (4) Date: Dec. 4, 2006

(87) PCT Pub. No.: WO2005/120585
PCT Pub. Date: Dec. 22, 2005

(65) Prior Publication Data
US 2007/0253899 A1    Nov. 1, 2007

Related U.S. Application Data

(60) Provisional application No. 60/577,142, filed on Jun. 4, 2004.

(51) Int. Cl.
| | | |
|---|---|---|
| *A61K 51/00* | (2006.01) | |
| *A61M 36/14* | (2006.01) | |
| *A61K 49/14* | (2006.01) | |
| *A61K 51/04* | (2006.01) | |
| *A61K 51/08* | (2006.01) | |
| *A61K 38/04* | (2006.01) | |
| *A61K 38/08* | (2006.01) | |
| *A61K 38/16* | (2006.01) | |

(52) U.S. Cl.
CPC ............. *A16K 49/1809* (2013.01); *A61K 49/14* (2013.01); *A61K 51/04* (2013.01); *A61K 51/08* (2013.01); *A61K 38/04* (2013.01); *A61K 38/08* (2013.01); *A61K 38/16* (2013.01)
USPC ........ 424/1.69; 424/1.11; 424/1.65; 530/300; 530/324; 530/325; 530/326; 530/327; 530/328; 530/329; 530/330

(58) Field of Classification Search
CPC . A61K 51/08; A61K 51/088; A61K 51/0478; A61K 51/06; A61K 51/0497; A61K 51/04; A61K 51/1282; A61K 51/00; A61K 51/02; A61K 2123/00; A61K 38/00; A61K 38/04; A61K 38/07; A61K 38/08; A61K 38/10; A61K 38/16; A61K 2121/00; A61K 49/00; A61K 49/06; A61K 49/10; A61K 49/18; A61K 49/101; A61K 49/14; A61K 49/12; A61K 49/103; A61K 49/105; A61K 49/106; A61K 49/108; C07K 14/00; C07K 4/00; C07K 7/08; C07K 7/06; C07K 7/00; C07K 7/04; C07K 5/00; C07K 5/10; C07K 5/12
USPC ........... 424/1.11, 1.13, 1.21, 1.29, 1.33, 1.37, 424/1.49, 1.65, 1.69, 1.81, 9, 1, 9.3, 9.4, 424/9.5, 9.6, 9.7, 9.8, 450, 1.73; 516/53, 516/20; 530/300, 324, 325, 326, 327, 328, 530/329, 330
See application file for complete search history.

(56) References Cited

U.S. PATENT DOCUMENTS

| | | | |
|---|---|---|---|
| 5,429,826 A * | 7/1995 | Nair et al. | 424/501 |
| 5,622,699 A | 4/1997 | Ruoslahti et al. | 424/93.6 |
| 6,068,829 A | 5/2000 | Ruoslahti et al. | 424/9.1 |
| 6,174,687 B1 | 1/2001 | Rajotte et al. | 435/7.1 |
| 6,180,084 B1 | 1/2001 | Ruoslahti et al. | 424/9.1 |
| 6,232,287 B1 | 5/2001 | Ruoslahti et al. | 514/2 |
| 6,296,832 B1 | 10/2001 | Ruoslahti et al. | 424/9.1 |
| 6,303,573 B1 | 10/2001 | Ruoslahti et al. | 514/12 |
| 6,306,365 B1 | 10/2001 | Ruoslahti et al. | 424/9.1 |
| 6,576,239 B1 | 6/2003 | Ruoslahti et al. | 424/185.1 |
| 7,204,997 B2 * | 4/2007 | Bromberg et al. | 424/487 |
| 2001/0046498 A1 | 11/2001 | Ruoslahti et al. | 424/178.1 |
| 2002/0041898 A1 | 4/2002 | Unger et al. | 424/486 |
| 2003/0008819 A1 | 1/2003 | Schnitzer | 514/12 |
| 2003/0049203 A1 | 3/2003 | Elmaleh et al. | 424/1.73 |
| 2003/0077826 A1 | 4/2003 | Edelman et al. | 435/440 |
| 2005/0025819 A1 | 2/2005 | Onyuksel et al. | 424/450 |

FOREIGN PATENT DOCUMENTS

WO         03/020751 A2      3/2003

OTHER PUBLICATIONS

Wu et al (Bioconjugate Chem., 2010, vol. 21, pp. 208-213).*
Zupancich et al (Biomacromolecules, 2009, vol. 10, No. 6, pp. 1554-1563).*
Lee et al (Journal of Controlled Release, 2004, vol. 94, pp. 323-335).*

* cited by examiner

*Primary Examiner* — D L Jones
(74) *Attorney, Agent, or Firm* — Renner, Otto, Boisselle & Sklar, LLP

(57) ABSTRACT

The invention relates to micelles that are elaborated with functionality useful for imaging and/or selectively targeting tissue, e.g., in the delivery of hydrophobic agents.

13 Claims, 8 Drawing Sheets

Preparation of cRGD-DOX-Micelles $^1$H NMR of MAL-PEG-PCL in CDCl$_3$

Synthesis of cRGD Using Solid Phase Peptide Synthesis Chemistry

Size characterization of 0% (A, B) and 76% (C, D) cRGD-DOX micelles by atomic force microscopy (A, C) and dynamic light scattering (B, D)

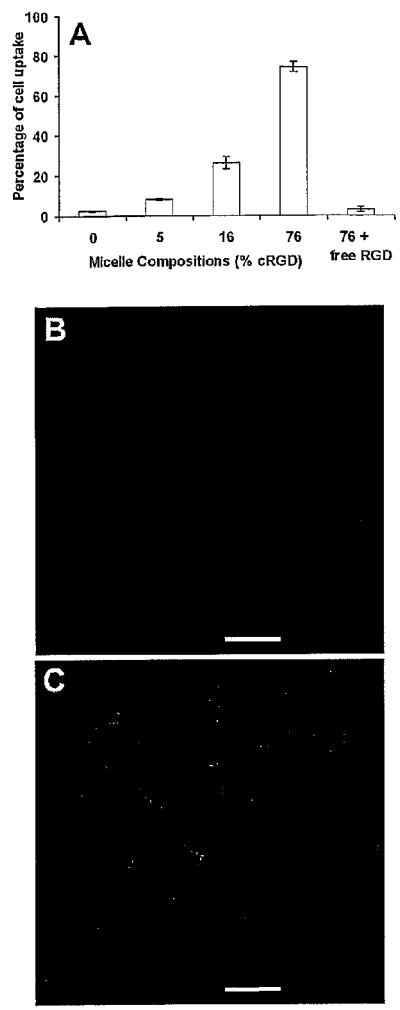

Figure 5

(A) Percentage of micelle uptake in SLK tumor endothelial cells measured by flow cytometry as a function of cRGD density (0-76%) on the micelle surface. The last panel shows that the cell uptake of 76% cRGD-micelles is inhibited by the presence of free RGD ligands (9 mM) in solution. (B, C) Confocal laser scanning microscopy images of SLK cells treated with 0% (B) and 16% (C) cRGD-micelles after incubation for 2 h. Cell nuclei were stained blue by Hoechst 33342 ($\lambda_{ex}$ = 352 nm, $\lambda_{em}$ = 455 nm) and overlaid with DOX fluorescent images ($\lambda_{ex}$ = 485 nm, $\lambda_{em}$ = 595 nm). The scale bars are 20 μm in both images Flow cytometry histogram of micelle uptake in SLK tumor endothelial cells as a function of cRGD density (A) 0% (B) 76% on the micelle surface. (C) Cell uptake of 76% cRGD-micelles is inhibited by the presence of free RGD ligands (9 mM) in solution Preparation of DOTA-PEG-b-PCL Micelles

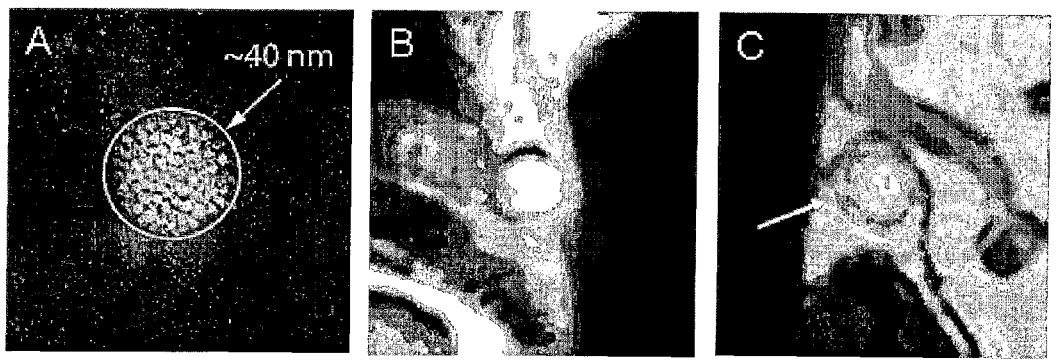

Figure 8

(A) Transmission electron micrograph (TEM) of a typical micelle containing numerous individual SPIO particles. The white circle denotes the approximate boundary of the micelle core. (B) $T_2$-weighted MRI image of a control mouse tumor. (C) $T_2$-weighted MRI image of a tumor 72 hours after micelle administration. The white arrow denotes the darkened rim of the tumor likely due to micelle accumulation

SEQUENCE LISTING

```
<160> NUMBER OF SEQ ID NOS: 758

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Leu Ser Ser Arg Leu Asp Ala Cys
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Val Leu Arg Gly Gly Arg Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Asn Ser Arg Leu Gln Leu Arg Cys
1               5

<210> SEQ ID NO 4
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 4

Cys Gly Val Arg Leu Gly Cys
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Lys Asp Trp Gly Arg Ile Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Leu Asp Trp Gly Arg Ile Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Thr Arg Ile Thr Glu Ser Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Glu Thr Leu Pro Ala Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Arg Thr Gly Thr Leu Phe Cys
1               5

<210> SEQ ID NO 10
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Gly Arg Ser Leu Asp Ala Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Arg His Trp Phe Asp Val Val Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ala Asn Ala Gln Ser His Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Gly Asn Pro Ser Tyr Arg Cys
1               5

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Arg Cys Val Leu Arg Glu Gly Pro Ala Gly Gly Cys Ala Trp Phe
1               5                   10                  15

Asn Arg His Arg Leu
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Tyr Pro Cys Gly Gly Glu Ala Val Ala Gly Val Ser Ser Val Arg Thr
1               5                   10                  15

Met Cys Ser Glu
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Asn Cys Asp Tyr Gln Gly Thr Asn Pro Ala Thr Ser Val Ser Val
1               5                   10                  15

Pro Cys Thr Val
            20

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Asn Ser Arg Leu His Leu Arg Cys Cys Glu Asn Trp Trp Gly Asp
1               5                   10                  15

Val Cys

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Arg Cys Val Leu Arg Glu Gly Pro Ala Gly Gly Cys Ala Trp Phe
1               5                   10                  15

Asn Arg His Arg Leu
            20

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Leu Pro Val Ala Ser Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Cys Gly Ala Arg Glu Met Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Lys Gly Arg Ser Ser Ala Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Trp Ala Arg Ala Gln Gly Cys
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Leu Gly Arg Ser Ser Val Cys
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Thr Ser Pro Gly Gly Ser Cys
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Cys Met Gly Arg Trp Arg Leu Cys
1               5

<210> SEQ ID NO 26
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 26

Cys Val Gly Glu Cys Gly Gly Cys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Val Ala Trp Leu Asn Cys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Arg Arg Phe Gln Asp Cys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Leu Met Gly Val His Cys
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Lys Leu Leu Ser Gly Val Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Phe Val Gly His Asp Leu Cys
1               5
```

```
<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Arg Cys Leu Asn Val Cys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Lys Leu Met Gly Glu Cys
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Gly Val Phe Trp Gln
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Gly Arg Val Arg Pro His
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Val Leu Val Thr Ser Ser
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Cys Leu His Arg Gly Asn Ser Cys
1               5

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Arg Ser Trp Asn Lys Ala Asp Asn Arg Ser Cys
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ala Gly Phe Phe Leu Val
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ser Gly Ala Arg Ser Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Val Glu Ser Thr Val Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Arg Arg Gln Pro Leu Ser
1               5

<210> SEQ ID NO 43
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 43

Ser Lys Val Trp Leu Leu Leu
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Val Arg Arg Val Pro Glu
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Ser Gly Lys Trp Gly Trp
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Val Gln Ser Val Gly
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Arg Ala Val Gly Arg Ala
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Ser Pro Gln Leu Ala Thr
1               5

<210> SEQ ID NO 49

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ala Val Leu Pro Gly Glu
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Ile Glu Glu Ala Glu Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Val Ser Glu Gln Leu Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Gly Asp Arg Pro Pro Tyr
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Arg Arg Gly Ser Pro Gln
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Val Arg Gly Pro Glu Arg
```

```
<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ile Ser Ala Val Leu Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Arg Gly Ser Trp Glu
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Val Ser Ala Ser Asp Trp
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Arg Val Arg Gly Ser Pro
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Arg Leu Ser Gly Gly Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Trp Glu Leu Val Ala Arg Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Arg Arg Asp Glu Gln Arg
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Cys Arg Cys Trp Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ser Pro Pro Tyr Met Trp
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Cys Thr Ala Met Thr Glu
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Arg Gly Asp Cys
1               5

<210> SEQ ID NO 66
<211> LENGTH: 6
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 66

Cys Arg Gly Asp Cys Leu
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Arg Gly Asp Cys Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Gly Arg Ala His Ala
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Gly Arg Ala His Ala
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Cys Asp Val Val Val
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Leu Ile Asp Ile Pro
1               5
```

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Ile Arg Ser Val Asp
1               5

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Arg Gly Asp
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Arg Gly Asp
1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Gly Asp Leu
1

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Ser Phe Gly Arg Gly Asp Ile Arg Asn Cys
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Ser Phe Gly Arg Thr Asp Gln Arg Ile Cys
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Ser Phe Gly Lys Gly Asp Asn Arg Ile Cys
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Ser Phe Gly Arg Asn Asp Ser Arg Asn Cys
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Ser Phe Gly Arg Val Asp Asp Arg Asn Cys
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Ser Phe Gly Arg Ala Asp Arg Arg Asn Cys
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Ser Phe Gly Arg Ser Val Asp Arg Asn Cys
1               5                   10

<210> SEQ ID NO 83
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 83

Cys Ser Phe Gly Lys Arg Asp Met Arg Asn Cys
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Ser Phe Gly Arg Trp Asp Ala Arg Asn Cys
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Ser Phe Gly Arg Gln Asp Val Arg Asn Cys
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Ser Phe Gly Arg Asp Asp Gly Arg Asn Cys
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Asp Cys Arg Gly Asp Cys Phe Cys
1               5

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Asn Gly Arg Cys Val Ser Gly Cys Ala Gly Arg Cys
1               5                   10

<210> SEQ ID NO 89

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Val Arg Ser Arg Leu Ser
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Val Gly Leu Val Ala Arg
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Val Lys Asp Tyr Phe Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Val Arg Thr Ser Ile Trp
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Pro Val Gly Met Arg Lys
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Val Arg Leu Val Asn Leu
```

```
<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Phe Ala Ala Val Arg Ser
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Leu Val Asn Ser Ser Trp
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Cys Glu Arg Val Trp Arg
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Phe Gly Ser Gln Ala Phe Val
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Trp Leu Glu Arg Pro Glu Tyr
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 100

Gly Gly Asp Val Met Trp Arg
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Val Arg Ala Arg Leu Met Ser
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Leu Arg Glu Ser Gly Pro
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Leu Ser Gly Gly Arg Ser
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Trp Cys Glu Pro Gly Trp Cys Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Glu Val Gln Ser Ala Lys Trp
1               5

<210> SEQ ID NO 106
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 106

Lys Arg Val Tyr Val Leu Gly
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Arg Leu Ser Val Gln Val
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Trp Lys Pro Ala Ser Leu Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Phe Ala Val Arg Val Val Gly
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Val Arg Pro Leu Glu Gly
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Phe Tyr Arg Met Leu Gly
1               5
```

```
<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Glu Gly Arg Pro Met Val Tyr
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Ser Arg Ser Leu Gly Ala
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Val Trp Gln Gly Asp Val
1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Asp Glu Leu Leu Ala
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Phe Val Trp Leu Val Gly Ser
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117
```

```
Gly Ser Glu Pro Met Phe Arg
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Val Ser Phe Leu Glu Tyr Arg
1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp His Gln Pro Leu
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser Met Ser Ile Ala Arg Leu
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Gly Arg Trp Leu Ala Leu
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Val Glu Glu Phe Pro Cys
1               5

<210> SEQ ID NO 123
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 123

Leu Trp Leu Ser Gly Asn Trp
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Pro Met Leu Ser Val Met
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Trp Thr Phe Leu Glu Arg Leu
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Leu Pro Gly Gly Gln Trp
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Glu Val Lys Glu Ser
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Thr Pro Ala Ala Val Met
1               5

<210> SEQ ID NO 129

```
<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Glu Trp Leu Gly Glu Cys
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Pro Asn Pro Leu Met Pro Leu
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Leu Trp Tyr Leu Gly Ala
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Val Gly Gly Trp Glu Leu
1               5

<210> SEQ ID NO 133
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Gly Phe Glu Cys Val Arg Gln Cys Pro Glu Arg Cys
1               5                   10

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Thr Leu Arg Asp Arg Asn Cys
```

```
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Ile Lys Gly Asn Val Asn Cys
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Arg His Glu Ser Ser Ser Cys
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Leu Tyr Ile Asp Arg Arg Cys
1               5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Cys Tyr Ser Leu Gly Ala Asp Cys
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Cys Ser Lys Leu Met Met Thr Cys
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 140

Cys Gly Phe Glu Leu Glu Thr Cys
1               5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Asn Ser Asp Val Asp Leu Cys
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Val Gly Asn Leu Ser Met Cys
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Glu Lys Lys Leu Leu Tyr Cys
1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Lys Gly Gln Arg Asp Phe Cys
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Thr Phe Arg Asn Ala Ser Cys
1               5

<210> SEQ ID NO 146
<211> LENGTH: 8
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 146

Cys Asn Met Gly Leu Thr Arg Cys
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Cys His Glu Gly Tyr Leu Thr Cys
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Cys Gly Thr Phe Gly Ala Arg Cys
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Cys Ile Gly Glu Val Glu Val Cys
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Arg Ile Ser Ala His Pro Cys
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Cys Leu Arg Pro Tyr Leu Asn Cys
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Cys Ser Tyr Pro Lys Ile Leu Cys
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Cys Met Glu Leu Ser Lys Gln Cys
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Cys Ser Glu Pro Ser Gly Thr Cys
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Cys Gly Asn Glu Thr Leu Arg Cys
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Thr Leu Ser Asn Arg Phe Cys
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Cys Met Gly Ser Glu Tyr Trp Cys
1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Leu Phe Ser Asp Glu Asn Cys
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Ala His Gln His Ile Gln Cys
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Lys Gly Gln Gly Asp Trp Cys
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Ala Gln Asn Met Leu Cys Cys
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Trp Arg Gly Asp Arg Lys Ile Cys
1               5

<210> SEQ ID NO 163
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 163

Cys Leu Ala Lys Glu Asn Val Val Cys
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Ile Phe Arg Glu Ala Asn Val Cys
1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Arg Thr His Gly Tyr Gln Gly Cys
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Glu Arg Val Val Gly Ser Ser Cys
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Cys Lys Thr Asn His Met Glu Ser Cys
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Tyr Glu Glu Lys Ser Gln Ser Cys
1               5

<210> SEQ ID NO 169
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Cys Lys Asp Ser Ala Met Thr Ile Cys
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Cys Thr Arg Ser Thr Asn Thr Gly Cys
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Cys Met Ser Trp Asp Ala Val Ser Cys
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys Lys Trp Ser Arg Leu His Ser Cys
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Cys Met Ser Pro Gln Arg Ser Asp Cys
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Leu His Ser Pro Arg Ser Lys Cys
```

```
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Cys Pro Gln Asp Ile Arg Arg Asn Cys
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Leu Tyr Thr Lys Glu Gln Arg Cys
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Gln Thr Arg Asn Phe Ala Gln Cys
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Thr Gly His Leu Ser Thr Asp Cys
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Cys Gln Asp Leu Asn Ile Met Gln Cys
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 180

Thr Arg Arg Thr Asn Asn Pro Leu Thr
1               5

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Cys Gly Tyr Ile Asp Pro Asn Arg Ile Ser Gln Cys
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Thr Val Asn Glu Ala Tyr Lys Thr Arg Met Cys
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Arg Leu Arg Ser Tyr Gly Thr Leu Ser Leu Cys
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Ala Gly Thr Cys Ala Thr Gly Cys Asn Gly Val Cys
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Cys Ala Asp Tyr Asp Leu Ala Leu Gly Leu Met Cys
1               5                   10

<210> SEQ ID NO 186
<211> LENGTH: 12
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 186

Cys Pro Lys Ala Arg Pro Ala Pro Gln Tyr Lys Cys
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Cys Ser Ser His Gln Gly Gly Phe Gln His Gly Cys
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Gln Glu Thr Arg Thr Glu Gly Arg Lys Lys Cys
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Cys Arg Pro Trp His Asn Gln Ala His Thr Glu Cys
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Cys Ser Phe Gly Thr His Asp Thr Glu Pro His Cys
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Cys Ser Glu Ala Ala Ser Arg Met Ile Gly Val Cys
1               5                   10

```
<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Cys Trp Glu Glu His Pro Ser Ile Lys Trp Trp Cys
1               5                   10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Trp Asp Ala Asp Gln Ile Glu Gly Ile Lys Cys
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Val Asp Ser Gln Ser Met Lys Gly Leu Val Cys
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Cys Arg Leu Gln Thr Met Gly Gln Gly Gln Ser Cys
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Arg Pro Ala Gln Arg Asp Ala Gly Thr Ser Cys
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197
```

```
Cys Gly Gly Arg Asp Arg Gly Thr Tyr Gly Pro Cys
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Cys Gly Glu Val Ala Ser Asn Glu Arg Ile Gln Cys
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Cys Asn Ser Lys Ser Ser Ala Glu Leu Glu Lys Cys
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Cys Val Leu Asn Phe Lys Asn Gln Ala Arg Asp Cys
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Cys Arg Gly Lys Pro Leu Ala Asn Phe Glu Asp Cys
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Cys Glu Gly His Ser Met Arg Gly Tyr Gly Leu Cys
1               5                   10

<210> SEQ ID NO 203
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 203

Cys Arg Asp Arg Gly Asp Arg Met Lys Ser Leu Cys
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Cys Asp Asn Thr Cys Thr Tyr Gly Val Asp Asp Cys
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Ser Ala His Ser Gln Glu Met Asn Val Asn Cys
1               5                   10

<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Cys Gly Ala Ala Cys Gly Val Gly Cys Arg Gly Arg Cys
1               5                   10

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Cys Gly Phe Glu Cys Val Arg Gln Cys Pro Glu Arg Cys
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Cys Leu Val Gly Cys Arg Leu Ser Cys Gly Gly Glu Cys
1               5                   10

<210> SEQ ID NO 209

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Cys Arg Ser Gly Cys Val Glu Gly Cys Gly Gly Arg Cys
1               5                   10

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Cys Ile Ala Arg Cys Gly Gly Ala Cys Gly Arg His Cys
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Cys Gly Gly Glu Cys Gly Trp Glu Cys Glu Val Ser Cys
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Cys Gly Val Gly Cys Pro Gly Leu Cys Gly Gly Ala Cys
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Cys Lys Trp Leu Cys Leu Leu Leu Cys Ala Val Ala Cys
1               5                   10

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Cys Ser Glu Gly Cys Gly Pro Val Cys Trp Pro Glu Cys
```

```
1               5                  10
```

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Cys Gly Ala Ala Cys Gly Val Gly Cys Gly Gly Arg Cys
1               5                  10
```

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Cys Ser Gly Ser Cys Arg Arg Gly Cys Gly Ile Asp Cys
1               5                  10
```

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Cys Gly Ala Ser Cys Ala Leu Gly Cys Arg Ala Tyr Cys
1               5                  10
```

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Cys Asp Thr Ser Cys Glu Asn Asn Cys Gln Gly Pro Cys
1               5                  10
```

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Cys Ser Arg Gln Cys Arg Gly Ala Cys Gly Gln Pro Cys
1               5                  10
```

<210> SEQ ID NO 220
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 220

Cys Tyr Trp Trp Cys Asp Gly Val Cys Ala Leu Gln Cys
1               5                   10

<210> SEQ ID NO 221
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Cys Ala Gly Gly Cys Ala Val Arg Cys Gly Gly Thr Cys
1               5                   10

<210> SEQ ID NO 222
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Cys Gly Gly Ala Cys Gly Gly Val Cys Thr Gly Gly Cys
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Cys Gly Arg Pro Cys Val Gly Glu Cys Arg Met Gly Cys
1               5                   10

<210> SEQ ID NO 224
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Cys Leu Val Gly Cys Glu Val Gly Cys Ser Pro Ala Cys
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Cys Pro Arg Thr Cys Gly Ala Ala Cys Ala Ser Pro Cys
1               5                   10

<210> SEQ ID NO 226
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 226

Cys Arg Gly Asp Cys Gly Ile Gly Cys Arg Arg Leu Cys
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Cys Cys Phe Thr Asn Phe Asp Cys Tyr Leu Gly Cys
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Cys Tyr Ala Asp Cys Glu Gly Thr Cys Gly Met Val Cys
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Cys Trp Asn Ile Cys Pro Gly Gly Cys Arg Ala Leu Cys
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gly Pro Gly Cys Glu Glu Glu Cys Gln Pro Ala Cys
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Cys Lys Gly Thr Cys Val Leu Gly Cys Ser Glu Glu Cys
1               5                   10
```

```
<210> SEQ ID NO 232
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Cys Ser Thr Leu Cys Gly Leu Arg Cys Met Gly Thr Cys
1               5                   10

<210> SEQ ID NO 233
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Cys Met Pro Arg Cys Gly Val Asn Cys Lys Trp Ala Cys
1               5                   10

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Cys Val Gly Ala Cys Asp Leu Lys Cys Thr Gly Gly Cys
1               5                   10

<210> SEQ ID NO 235
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Cys Val Ala Leu Cys Arg Glu Ala Cys Gly Glu Gly Cys
1               5                   10

<210> SEQ ID NO 236
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Cys Ser Ser Gly Cys Ser Lys Asn Cys Leu Glu Met Cys
1               5                   10

<210> SEQ ID NO 237
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237
```

```
Cys Gly Arg Pro Cys Arg Gly Gly Cys Ala Ala Ser Cys
1               5                   10
```

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Cys Gln Gly Gly Cys Gly Val Ser Cys Pro Ile Phe Cys
1               5                   10
```

<210> SEQ ID NO 239
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

```
Cys Ala Val Arg Cys Asp Gly Ser Cys Val Pro Glu Cys
1               5                   10
```

<210> SEQ ID NO 240
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

```
Cys Gly Phe Gly Cys Ser Gly Ser Cys Gln Met Gln Cys
1               5                   10
```

<210> SEQ ID NO 241
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

```
Cys Arg Val Val Cys Ala Asp Gly Cys Arg Phe Ile Cys
1               5                   10
```

<210> SEQ ID NO 242
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

```
Cys Thr Met Gly Cys Thr Ala Gly Cys Ala Phe Ala Cys
1               5                   10
```

<210> SEQ ID NO 243
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 243

Cys Glu Gly Lys Cys Gly Leu Thr Cys Glu Cys Thr Cys
1               5                   10

<210> SEQ ID NO 244
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Cys Asn Gln Gly Cys Ser Gly Ser Cys Asp Val Met Cys
1               5                   10

<210> SEQ ID NO 245
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Cys Ala Ser Gly Cys Ser Glu Ser Cys Tyr Val Gly Cys
1               5                   10

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Cys Gly Gly Gly Cys Gln Trp Gly Cys Ala Gly Glu Cys
1               5                   10

<210> SEQ ID NO 247
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Cys Ser Val Arg Cys Lys Ser Val Cys Ile Gly Leu Cys
1               5                   10

<210> SEQ ID NO 248
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Pro Ser Asn Cys Val Ala Leu Cys Thr Ser Gly Cys
1               5                   10

<210> SEQ ID NO 249

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Cys Val Glu Gly Cys Ser Ser Gly Cys Gly Pro Gly Cys
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Arg Val Val Cys Ala Asp Gly Cys Arg Leu Ile Cys
1               5                   10

<210> SEQ ID NO 251
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Ser Thr Leu Cys Gly Leu Arg Cys Met Gly Thr Cys
1               5                   10

<210> SEQ ID NO 252
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Cys Phe Thr Phe Cys Glu Tyr His Cys Gln Leu Thr Cys
1               5                   10

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Cys Arg Arg Ile Trp Tyr Ala Val Cys
1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Cys Ser Ala Tyr Thr Thr Ser Pro Cys
```

```
<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Cys Ser Cys Phe Arg Asp Val Cys Cys
1               5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Cys Thr Asp Lys Ser Trp Pro Cys
1               5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Cys Thr Asp Asn Arg Val Gly Ser
1               5

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Thr Ile Ala Asp Phe Pro Cys
1               5

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Cys Thr Ser Asp Ile Ser Trp Trp Asp Tyr Lys Cys
1               5                   10

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 260

Cys Thr Val Asp Asn Glu Leu Cys
1               5

<210> SEQ ID NO 261
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Cys Val Gly Asp Cys Ile Gly Ser Cys Trp Met Phe Cys
1               5                   10

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Val Lys Phe Thr Tyr Asp Cys
1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Cys Val Ser Gly His Leu Asn Cys
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Cys Tyr Gly Glu Ser Gln Gln Met Cys
1               5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Cys Tyr Thr Gly Glu Thr Trp Thr Cys
1               5

<210> SEQ ID NO 266
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 266

Cys Ala Val Ser Ile Pro Arg Cys
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Cys Asp Cys Arg Gly Asp Cys Phe Cys
1               5

<210> SEQ ID NO 268
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Cys Asp Ser Leu Cys Gly Gly Ala Cys Ala Ala Arg Cys
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Cys Glu Arg Ser Gln Ser Lys Gly Val His His Cys
1               5                   10

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Cys Phe Lys Ser Thr Leu Leu Cys
1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Cys Phe Trp His Asn Arg Ala Cys
1               5
```

```
<210> SEQ ID NO 272
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Cys Gly Asp Val Cys Pro Ser Glu Cys Pro Gly Trp Cys
1               5                   10

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Cys Gly Glu Phe Lys Val Gly Cys
1               5

<210> SEQ ID NO 274
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Cys Gly Leu Asp Cys Leu Gly Asp Cys Ser Gly Ala Cys
1               5                   10

<210> SEQ ID NO 275
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Cys Gly Pro Gly Tyr Gln Ala Gln Cys Ser Leu Arg Cys
1               5                   10

<210> SEQ ID NO 276
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Cys Gly Ser His Cys Gly Gln Leu Cys Lys Ser Leu Cys
1               5                   10

<210> SEQ ID NO 277
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277
```

```
Cys His Met Gly Cys Val Ser Pro Cys Ala Tyr Val Cys
1               5                   10
```

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

```
Cys Ile Leu Ser Tyr Asp Asn Pro Cys
1               5
```

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

```
Cys Ile Ser Arg Pro Tyr Phe Cys
1               5
```

<210> SEQ ID NO 280
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

```
Cys Lys Glu Arg Leu Glu Tyr Thr Arg Gly Val Cys
1               5                   10
```

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

```
Cys Lys Glu Arg Pro Ser Asn Gly Leu Ser Ala Cys
1               5                   10
```

<210> SEQ ID NO 282
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

```
Cys Lys Pro Phe Arg Thr Glu Cys
1               5
```

<210> SEQ ID NO 283
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 283

Cys Lys Ser Gly Cys Gly Val Ala Cys Arg His Met Cys
1               5                   10

<210> SEQ ID NO 284
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Cys Leu Lys Pro Gly Gly Gln Glu Cys
1               5

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Cys Met Asp Ser Gln Ser Ser Cys
1               5

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Cys Met Asn Ile Leu Ser Gly Cys
1               5

<210> SEQ ID NO 287
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Cys Asn Ile Pro Val Thr Thr Pro Ile Phe Gly Cys
1               5                   10

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Cys Asn Gln Arg Thr Asn Arg Glu Ser Gly Asn Cys
1               5                   10

<210> SEQ ID NO 289

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Cys Asn Arg Lys Asn Ser Asn Glu Gln Arg Ala Cys
1               5                   10

<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Cys Asn Arg Met Glu Met Pro Cys
1               5

<210> SEQ ID NO 291
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Cys Gln Ile Arg Pro Ile Asp Lys Cys
1               5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Cys Ala Ile Asp Ile Gly Gly Ala Cys
1               5

<210> SEQ ID NO 293
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Cys Gly Arg Phe Asp Thr Ala Pro Gln Arg Gly Cys
1               5                   10

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Cys Lys Arg Ala Asn Arg Leu Ser Cys
```

-continued

```
1               5

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Cys Leu Leu Asn Tyr Thr Tyr Cys
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Cys Leu Asn Gly Leu Val Ser Met Cys
1               5

<210> SEQ ID NO 297
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Cys Met Ser Leu Gly Asn Asn Cys
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Cys Asn Arg Asn Arg Met Thr Pro Cys
1               5

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Cys Gln Ala Ser Ala Ser Asp His Cys
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 300

Cys Gln Leu Ile Asn Ser Ser Pro Cys
1               5

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Cys Gln Arg Val Asn Ser Val Glu Asn Ala Ser Cys
1               5                   10

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Cys Arg Lys Glu His Tyr Pro Cys
1               5

<210> SEQ ID NO 303
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Cys Arg Arg His Met Glu Arg Cys
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Cys Ser Gly Arg Pro Phe Lys Tyr Cys
1               5

<210> SEQ ID NO 305
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Cys Thr His Leu Val Thr Leu Cys
1               5

<210> SEQ ID NO 306
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 306

Cys Thr Ser Ser Pro Ala Tyr Asn Cys
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Cys Val Thr Ser Asn Leu Arg Val Cys
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Cys Trp Asp Ser Gly Ser His Ile Cys
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Cys Glu Arg Ser His Gly Arg Leu Cys
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Cys Gly Asn Leu Leu Thr Arg Arg Cys
1               5

<210> SEQ ID NO 311
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Cys Ile Asn Cys Leu Ser Gln Cys
1               5
```

```
<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Cys Leu Arg His Asp Phe Tyr Val Cys
1               5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Cys Asn Ser Arg Ser Glu Asn Cys
1               5

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Cys Arg Tyr Lys Gly Pro Ser Cys
1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Cys Ser His His Asp Thr Asn Cys
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Cys Ser Arg Trp Tyr Thr Thr Cys
1               5

<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317
```

```
Cys Tyr Ala Gly Ser Pro Leu Cys
1               5

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Cys Gln Thr Thr Ser Trp Asn Cys
1               5

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Cys Gln Trp Ser Met Asn Val Cys
1               5

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Cys Arg Ala Arg Ile Arg Ala Glu Asp Ile Ser Cys
1               5                   10

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Cys Arg Asp Val Val Ser Val Ile Cys
1               5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Cys Arg Arg Glu Tyr Ser Ala Cys
1               5

<210> SEQ ID NO 323
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 323

Glu Ile Cys Gln Leu Gly Ser Cys Thr
1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Trp Arg Cys Glu Gly Phe Asn Cys Gln
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Arg Lys Cys Leu Arg Pro Asp Cys Gly
1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Ser Trp Cys Glu Pro Gly Trp Cys Arg
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Leu Ala Cys Phe Val Thr Gly Cys Leu
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gly Leu Cys Asn Gly Ala Thr Cys Met
1               5

<210> SEQ ID NO 329

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Asp Met Cys Trp Leu Ile Gly Cys Gly
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Gly Cys Arg Thr Met Val Cys Val
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Arg Cys Pro Arg Ser Phe Cys Leu
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Leu Ser Cys Ala Pro Val Ile Cys Gly
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Arg Glu Cys Thr Asn Glu Ile Cys Tyr
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asn Glu Cys Leu Met Ile Ser Cys Arg
```

<210> SEQ ID NO 335
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ser Cys Val Phe Cys Asp Trp Leu Ser
1               5

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Trp Ala Cys Glu Glu Leu Ser Cys Phe
1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Gln Asn Cys Pro Val Thr Arg Cys Val
1               5

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Cys Ala Thr Leu Thr Asn Asp Glu Cys
1               5

<210> SEQ ID NO 339
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Cys Asp Asn Arg Glu Met Ser Cys
1               5

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 340

Cys Phe Met Asp His Ser Asn Cys
1               5

<210> SEQ ID NO 341
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Cys Gly Glu Tyr Gly Arg Glu Cys
1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Cys His Met Lys Arg Asp Arg Thr Cys
1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Cys Lys Lys Arg Leu Leu Asn Val Cys
1               5

<210> SEQ ID NO 344
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Cys Leu Asp Tyr His Pro Lys Cys
1               5

<210> SEQ ID NO 345
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Cys Met Thr Gly Arg Val Thr Cys
1               5

<210> SEQ ID NO 346
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 346

Cys Asn Lys Ile Val Arg Arg Cys
1               5

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Cys Pro Asp Leu Leu Val Ala Cys
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Cys Ser Asp Thr Gln Ser Ile Gly Cys
1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Cys Ser Lys Ala Tyr Asp Leu Ala Cys
1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Cys Ser Lys Lys Gly Pro Ser Tyr Cys
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Cys Thr Leu Lys His Thr Ala Met Cys
1               5
```

```
<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Cys Thr Gln His Ile Ala Asn Cys
1               5

<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Cys Thr Thr Glu Ile Asp Tyr Cys
1               5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Cys Val Gly Arg Ser Gly Glu Leu Cys
1               5

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ala Arg Arg Gly Trp Thr Leu
1               5

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ser Arg Arg Phe Val Gly Gly
1               5

<210> SEQ ID NO 357
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357
```

```
Gln Leu Thr Gly Gly Cys Leu
1               5

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ala Leu Glu Arg Arg Ser Leu
1               5

<210> SEQ ID NO 359
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Lys Ala Tyr Phe Arg Trp Arg
1               5

<210> SEQ ID NO 360
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Arg Trp Leu Ala Trp Thr Val
1               5

<210> SEQ ID NO 361
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Val Gly Ser Phe Ile Tyr Ser
1               5

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Leu Ser Leu Leu Gly Ile Ala
1               5

<210> SEQ ID NO 363
<211> LENGTH: 7
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 363

Leu Ser Thr Val Leu Trp Phe
1               5

<210> SEQ ID NO 364
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ser Leu Ala Met Arg Asp Ser
1               5

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Gly Arg Ser Ser Leu Ala Cys
1               5

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ser Glu Leu Leu Gly Asp Ala
1               5

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Cys Gly Gly Ala Gly Ala Arg
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Trp Arg Gln Asn Met Pro Leu
1               5

<210> SEQ ID NO 369

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Asp Phe Leu Arg Cys Arg Val
1               5

<210> SEQ ID NO 370
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gln Ala Gly Leu Arg Cys His
1               5

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Arg Ala Leu Tyr Asp Ala Leu
1               5

<210> SEQ ID NO 372
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Trp Val Ser Val Leu Gly Phe
1               5

<210> SEQ ID NO 373
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gly Met Ala Val Ser Ser Trp
1               5

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ser Trp Phe Phe Leu Val Ala
```

```
1               5

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Trp Gln Ser Val Val Arg Val
1               5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Val Lys Ser Val Cys Arg Thr
1               5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Cys Gly Asn Gly His Ser Cys
1               5

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ala Glu Met Glu Gly Arg Asp
1               5

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ser Leu Arg Pro Asp Asn Gly
1               5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 380

Pro Ala Met Gly Leu Ile Arg
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Trp Gly Cys Lys Leu Arg Phe Cys Ser
1               5

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Met Glu Cys Ile Lys Tyr Ser Cys Leu
1               5

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Gly Ile Cys Ala Thr Val Lys Cys Ser
1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Pro Arg Cys Gln Leu Trp Ala Cys Thr
1               5

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Thr Thr Cys Met Ser Gln Leu Cys Leu
1               5

<210> SEQ ID NO 386
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 386

Ser His Cys Pro Met Ala Ser Leu Cys
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gly Cys Val Arg Arg Leu Leu Cys Asn
1               5

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Thr Ser Cys Arg Leu Phe Ser Cys Ala
1               5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Lys Tyr Cys Thr Pro Val Glu Cys Leu
1               5

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Gly Cys Asn Gly Ser Arg Cys Ser
1               5

<210> SEQ ID NO 391
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Met Cys Pro Gln Arg Asn Cys Leu
1               5
```

```
<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Pro Glu Cys Glu Gly Val Ser Cys Ile
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ala Gly Cys Ser Val Thr Val Cys Gly
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ile Pro Cys Tyr Trp Glu Ser Cys Arg
1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gly Ser Cys Ser Met Phe Pro Cys Ser
1               5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gln Asp Cys Val Lys Arg Pro Cys Val
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397
```

Ser Glu Cys Ala Tyr Arg Ala Cys Ser
1               5

<210> SEQ ID NO 398
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Trp Ser Cys Ala Arg Pro Leu Cys Gly
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Ser Leu Cys Gly Ser Asp Gly Cys Arg
1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Arg Leu Cys Pro Ser Ser Pro Cys Thr
1               5

<210> SEQ ID NO 401
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Met Arg Cys Gln Phe Ser Gly Cys Thr
1               5

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Arg Tyr Cys Tyr Pro Asp Gly Cys Leu
1               5

<210> SEQ ID NO 403
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 403

Ser Thr Cys Gly Asn Trp Thr Cys Arg
1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Leu Pro Cys Thr Gly Ala Ser Cys Pro
1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Cys Ser Cys Thr Gly Gln Leu Cys Arg
1               5

<210> SEQ ID NO 406
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Leu Glu Cys Arg Arg Trp Arg Cys Asp
1               5

<210> SEQ ID NO 407
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Gly Leu Cys Gln Ile Asp Glu Cys Arg
1               5

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Thr Ala Cys Lys Val Ala Ala Cys His
1               5

<210> SEQ ID NO 409

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Asp Arg Cys Leu Asp Ile Trp Cys Leu
1               5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid

<400> SEQUENCE: 410

Xaa Xaa Xaa Gln Gly Ser Pro Cys Leu
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Pro Leu Cys Met Ala Thr Arg Cys Ala
1               5

<210> SEQ ID NO 412
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Arg Asp Cys Ser His Arg Ser Cys Glu
1               5

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Asn Pro Cys Leu Arg Ala Ala Cys Ile
1               5

<210> SEQ ID NO 414
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 414

Pro Thr Cys Ala Tyr Gly Trp Cys Ala
1               5

<210> SEQ ID NO 415
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Leu Glu Cys Val Ala Asn Leu Cys Thr
1               5

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Arg Lys Cys Gly Glu Glu Val Cys Thr
1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Glu Pro Cys Thr Trp Asn Ala Cys Leu
1               5

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Leu Val Cys Pro Gly Thr Ala Cys Val
1               5

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Leu Tyr Cys Leu Asp Ala Ser Cys Leu
1               5

<210> SEQ ID NO 420
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 420

Glu Arg Cys Pro Met Ala Lys Cys Tyr
1               5

<210> SEQ ID NO 421
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Leu Val Cys Gln Gly Ser Pro Cys Leu
1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Gln Gln Cys Gln Asp Pro Tyr Cys Leu
1               5

<210> SEQ ID NO 423
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 423

Asp Xaa Cys Xaa Asp Ile Trp Cys Leu
1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gln Pro Cys Arg Ser Met Val Cys Ala
1               5

<210> SEQ ID NO 425
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 425

Lys Thr Cys Val Gly Val Arg Val
1               5

<210> SEQ ID NO 426
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Trp Ser Cys His Glu Phe Asn Cys Arg
1               5

<210> SEQ ID NO 427
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Leu Thr Cys Trp Asp Trp Ser Cys Arg
1               5

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ser Leu Cys Arg Leu Ser Thr Cys Ser
1               5

<210> SEQ ID NO 429
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Lys Thr Cys Ala Gly Ser Ser Cys Ile
1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Val Ile Cys Thr Gly Arg Gln Cys Gly
1               5

<210> SEQ ID NO 431

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Asn Pro Cys Phe Gly Leu Leu Val
1               5

<210> SEQ ID NO 432
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ser Leu Cys Thr Ala Phe Asn Cys His
1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Arg Thr Cys Thr Pro Ser Arg Cys Met
1               5

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Gln Ser Cys Leu Trp Arg Ile Cys Ile
1               5

<210> SEQ ID NO 435
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Gln Tyr Cys Trp Ser Lys Gly Cys Arg
1               5

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Leu Gly Cys Phe Pro Ser Trp Cys Gly
```

```
<210> SEQ ID NO 437
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Val Thr Cys Ser Ser Glu Trp Cys Leu
1               5

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Arg Leu Cys Ser Trp Gly Gly Cys Ala
1               5

<210> SEQ ID NO 439
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Ser Thr Cys Ile Ser Val His Cys Ser
1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Glu Val Cys Leu Val Leu Ser Cys Gln
1               5

<210> SEQ ID NO 441
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Ile Ala Cys Asp Gly Tyr Leu Cys Gly
1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 442

Arg Asp Cys Val Lys Asn Leu Cys Arg
1               5

<210> SEQ ID NO 443
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 443

Xaa Gly Cys Tyr Gln Lys Arg Cys Thr
1               5

<210> SEQ ID NO 444
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 444

Leu Gly Cys Phe Xaa Ser Trp Cys Gly
1               5

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ile Arg Cys Trp Gly Gly Arg Cys Ser
1               5

<210> SEQ ID NO 446
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Ile Pro Cys Ser Leu Leu Gly Cys Ala
1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

```
Ala Gly Cys Val Gln Ser Gln Cys Tyr
1               5

<210> SEQ ID NO 448
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Pro Arg Cys Trp Glu Arg Val Cys Ser
1               5

<210> SEQ ID NO 449
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid

<400> SEQUENCE: 449

Lys Ala Cys Phe Gly Ala Asp Cys Xaa
1               5

<210> SEQ ID NO 450
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Thr Leu Cys Pro Leu Val Ala Cys Glu
1               5

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Ser Ala Cys Trp Leu Ser Asn Cys Ala
1               5

<210> SEQ ID NO 452
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Ser Glu Cys Tyr Thr Gly Ser Cys Pro
1               5

<210> SEQ ID NO 453
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Gly Leu Cys Gln Glu His Arg Cys Trp
1               5

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Val Glu Cys Gly Phe Ser Ala Val Phe
1               5

<210> SEQ ID NO 455
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Glu Asp Cys Arg Glu Trp Gly Cys Arg
1               5

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

His Trp Cys Arg Leu Leu Ala Cys Arg
1               5

<210> SEQ ID NO 457
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Trp Gly Cys Lys Leu Arg Phe Cys Ser
1               5

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Met Glu Cys Ile Lys Tyr Ser Cys Leu
```

-continued

```
<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Gly Ile Cys Ala Thr Val Lys Cys Ser
1               5

<210> SEQ ID NO 460
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Pro Arg Cys Gln Leu Trp Ala Cys Thr
1               5

<210> SEQ ID NO 461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Thr Thr Cys Met Ser Gln Leu Cys Leu
1               5

<210> SEQ ID NO 462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Ser His Cys Pro Met Ala Ser Leu Cys
1               5

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Gly Cys Val Arg Arg Leu Leu Cys Asn
1               5

<210> SEQ ID NO 464
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 464

Thr Ser Cys Arg Leu Phe Ser Cys Ala
1               5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Lys Tyr Cys Thr Pro Val Glu Cys Leu
1               5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Arg Gly Cys Asn Gly Ser Arg Cys Ser
1               5

<210> SEQ ID NO 467
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Met Cys Pro Gln Arg Asn Cys Leu
1               5

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Pro Glu Cys Glu Gly Val Ser Cys Ile
1               5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ala Gly Cys Ser Val Thr Val Cys Gly
1               5

<210> SEQ ID NO 470
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 470

Ile Pro Cys Tyr Trp Glu Ser Cys Arg
1               5

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Gly Ser Cys Ser Met Phe Pro Cys Ser
1               5

<210> SEQ ID NO 472
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Gln Asp Cys Val Lys Arg Pro Cys Val
1               5

<210> SEQ ID NO 473
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Ser Glu Cys Ala Tyr Arg Ala Cys Ser
1               5

<210> SEQ ID NO 474
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Trp Ser Cys Ala Arg Pro Leu Cys Gly
1               5

<210> SEQ ID NO 475
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Ser Leu Cys Gly Ser Asp Gly Cys Arg
1               5
```

<210> SEQ ID NO 476
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Arg Leu Cys Pro Ser Ser Pro Cys Thr
1               5

<210> SEQ ID NO 477
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Met Arg Cys Gln Phe Ser Gly Cys Thr
1               5

<210> SEQ ID NO 478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Arg Tyr Cys Tyr Pro Asp Gly Cys Leu
1               5

<210> SEQ ID NO 479
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Ser Thr Cys Gly Asn Trp Thr Cys Arg
1               5

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Leu Pro Cys Thr Gly Ala Ser Cys Pro
1               5

<210> SEQ ID NO 481
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

```
Cys Ser Cys Thr Gly Gln Leu Cys Arg
1               5
```

<210> SEQ ID NO 482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

```
Leu Glu Cys Arg Arg Trp Arg Cys Asp
1               5
```

<210> SEQ ID NO 483
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

```
Gly Leu Cys Gln Ile Asp Glu Cys Arg
1               5
```

<210> SEQ ID NO 484
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

```
Thr Ala Cys Lys Val Ala Ala Cys His
1               5
```

<210> SEQ ID NO 485
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

```
Asp Arg Cys Leu Asp Ile Trp Cys Leu
1               5
```

<210> SEQ ID NO 486
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid

<400> SEQUENCE: 486

```
Xaa Xaa Xaa Gln Gly Ser Pro Cys Leu
1               5
```

<210> SEQ ID NO 487

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Pro Leu Cys Met Ala Thr Arg Cys Ala
1               5

<210> SEQ ID NO 488
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Arg Asp Cys Ser His Arg Ser Cys Glu
1               5

<210> SEQ ID NO 489
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Asn Pro Cys Leu Arg Ala Ala Cys Ile
1               5

<210> SEQ ID NO 490
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Pro Thr Cys Ala Tyr Gly Trp Cys Ala
1               5

<210> SEQ ID NO 491
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Leu Glu Cys Val Ala Asn Leu Cys Thr
1               5

<210> SEQ ID NO 492
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Arg Lys Cys Gly Glu Glu Val Cys Thr
```

```
1               5

<210> SEQ ID NO 493
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Glu Pro Cys Thr Trp Asn Ala Cys Leu
1               5

<210> SEQ ID NO 494
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Leu Val Cys Pro Gly Thr Ala Cys Val
1               5

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Leu Tyr Cys Leu Asp Ala Ser Cys Leu
1               5

<210> SEQ ID NO 496
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Glu Arg Cys Pro Met Ala Lys Cys Tyr
1               5

<210> SEQ ID NO 497
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Leu Val Cys Gln Gly Ser Pro Cys Leu
1               5

<210> SEQ ID NO 498
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 498

Gln Gln Cys Gln Asp Pro Tyr Cys Leu
1               5

<210> SEQ ID NO 499
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 499

Asp Xaa Cys Xaa Asp Ile Trp Cys Leu
1               5

<210> SEQ ID NO 500
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Gln Pro Cys Arg Ser Met Val Cys Ala
1               5

<210> SEQ ID NO 501
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Lys Thr Cys Val Gly Val Arg Val
1               5

<210> SEQ ID NO 502
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Trp Ser Cys His Glu Phe Asn Cys Arg
1               5

<210> SEQ ID NO 503
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

```
Leu Thr Cys Trp Asp Trp Ser Cys Arg
1               5

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Ser Leu Cys Arg Leu Ser Thr Cys Ser
1               5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Lys Thr Cys Ala Gly Ser Ser Cys Ile
1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Val Ile Cys Thr Gly Arg Gln Cys Gly
1               5

<210> SEQ ID NO 507
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Asn Pro Cys Phe Gly Leu Leu Val
1               5

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Ser Leu Cys Thr Ala Phe Asn Cys His
1               5

<210> SEQ ID NO 509
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 509

Arg Thr Cys Thr Pro Ser Arg Cys Met
1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gln Ser Cys Leu Trp Arg Ile Cys Ile
1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Gln Tyr Cys Trp Ser Lys Gly Cys Arg
1               5

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Leu Gly Cys Phe Pro Ser Trp Cys Gly
1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Val Thr Cys Ser Ser Glu Trp Cys Leu
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Arg Leu Cys Ser Trp Gly Gly Cys Ala
1               5

<210> SEQ ID NO 515

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Ser Thr Cys Ile Ser Val His Cys Ser
1               5

<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Glu Val Cys Leu Val Leu Ser Cys Gln
1               5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Ile Ala Cys Asp Gly Tyr Leu Cys Gly
1               5

<210> SEQ ID NO 518
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Arg Asp Cys Val Lys Asn Leu Cys Arg
1               5

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 519

Xaa Gly Cys Tyr Gln Lys Arg Cys Thr
1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Any amino acid

<400> SEQUENCE: 520

Leu Gly Cys Phe Xaa Ser Trp Cys Gly
1               5

<210> SEQ ID NO 521
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Ile Arg Cys Trp Gly Gly Arg Cys Ser
1               5

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Ile Pro Cys Ser Leu Leu Gly Cys Ala
1               5

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Ala Gly Cys Val Gln Ser Gln Cys Tyr
1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Pro Arg Cys Trp Glu Arg Val Cys Ser
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any amino acid

<400> SEQUENCE: 525
```

```
Lys Ala Cys Phe Gly Ala Asp Cys Xaa
1               5

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Thr Leu Cys Pro Leu Val Ala Cys Glu
1               5

<210> SEQ ID NO 527
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Ser Ala Cys Trp Leu Ser Asn Cys Ala
1               5

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Ser Glu Cys Tyr Thr Gly Ser Cys Pro
1               5

<210> SEQ ID NO 529
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Gly Leu Cys Gln Glu His Arg Cys Trp
1               5

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Val Glu Cys Gly Phe Ser Ala Val Phe
1               5

<210> SEQ ID NO 531
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 531

Glu Asp Cys Arg Glu Trp Gly Cys Arg
1               5

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

His Trp Cys Arg Leu Leu Ala Cys Arg
1               5

<210> SEQ ID NO 533
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Leu Met Leu Pro Arg Ala Asp
1               5

<210> SEQ ID NO 534
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Cys Gly Arg Glu Cys Pro Arg Leu Cys Gln Ser Ser Cys
1               5                   10

<210> SEQ ID NO 535
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Cys Gly Glu Ala Cys Gly Gly Gln Cys Ala Leu Pro Cys
1               5                   10

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Pro Ser Cys Ala Tyr Met Cys Ile Thr
1               5

<210> SEQ ID NO 537

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Ser Lys Val Leu Tyr Tyr Asn Trp Glu
1               5

<210> SEQ ID NO 538
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Cys Glu Arg Ala Cys Arg Asn Leu Cys Arg Glu Gly Cys
1               5                   10

<210> SEQ ID NO 539
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Cys Lys Val Cys Asn Gly Arg Cys Cys Gly
1               5                   10

<210> SEQ ID NO 540
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Cys Pro Thr Cys Asn Gly Arg Cys Val Arg
1               5                   10

<210> SEQ ID NO 541
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Cys Arg Asn Cys Asn Gly Arg Cys Glu Gly
1               5                   10

<210> SEQ ID NO 542
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Cys Thr Glu Cys Asn Gly Arg Cys Gln Leu
```

<210> SEQ ID NO 543
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Cys Ala Val Cys Asn Gly Arg Cys Gly Phe
1               5                   10

<210> SEQ ID NO 544
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Cys Trp Gly Cys Asn Gly Arg Cys Arg Met
1               5                   10

<210> SEQ ID NO 545
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Cys Val Pro Cys Asn Gly Arg Cys His Glu
1               5                   10

<210> SEQ ID NO 546
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Cys Val Gln Cys Asn Gly Arg Cys Ala Leu
1               5                   10

<210> SEQ ID NO 547
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Cys Gly Arg Cys Asn Gly Arg Cys Leu Leu
1               5                   10

<210> SEQ ID NO 548
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 548

Cys Val Trp Cys Asn Gly Arg Cys Gly Leu
1               5                   10

<210> SEQ ID NO 549
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Cys Glu Gly Val Asn Gly Arg Arg Leu Arg
1               5                   10

<210> SEQ ID NO 550
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Cys Gly Ser Leu Val Arg Cys
1               5

<210> SEQ ID NO 551
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Ser Lys Gly Leu Arg His Arg
1               5

<210> SEQ ID NO 552
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Lys Met Gly Pro Lys Val Trp
1               5

<210> SEQ ID NO 553
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Asn Pro Arg Trp Phe Trp Asp
1               5

<210> SEQ ID NO 554
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 554

Ser Gly Trp Cys Tyr Arg Cys
1               5

<210> SEQ ID NO 555
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Cys Trp Ser Gly Val Asp Cys
1               5

<210> SEQ ID NO 556
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Ile Val Ala Asp Tyr Gln Arg
1               5

<210> SEQ ID NO 557
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Leu Ser Met Phe Thr Arg Pro
1               5

<210> SEQ ID NO 558
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Cys Val Met Val Arg Asp Gly Asp Cys
1               5

<210> SEQ ID NO 559
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Cys Gly Val Gly Ser Ser Cys
1               5
```

<210> SEQ ID NO 560
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Cys Gly Glu Gly His Pro Cys
1               5

<210> SEQ ID NO 561
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Cys Pro Glu His Arg Ser Leu Val Cys
1               5

<210> SEQ ID NO 562
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Cys Trp Arg Lys Phe Tyr Cys
1               5

<210> SEQ ID NO 563
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Cys Pro Arg Gly Ser Arg Cys
1               5

<210> SEQ ID NO 564
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Cys Ala Gln Leu Leu Gln Val Ser Cys
1               5

<210> SEQ ID NO 565
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

```
Cys Thr Asp Tyr Val Arg Cys
1               5

<210> SEQ ID NO 566
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Thr Asp Cys Thr Pro Ser Arg Cys Thr
1               5

<210> SEQ ID NO 567
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Cys Thr Ala Met Arg Asn Thr Asp Cys
1               5

<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Val Thr Cys Arg Ser Leu Met Cys Gln
1               5

<210> SEQ ID NO 569
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Cys Ile Ser Leu Asp Arg Ser Cys
1               5

<210> SEQ ID NO 570
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Cys Tyr Leu Val Asn Val Asp Cys
1               5

<210> SEQ ID NO 571
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 571

Arg His Cys Phe Ser Gln Trp Cys Ser
1               5

<210> SEQ ID NO 572
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Glu Ala Cys Glu Met Ala Gly Cys Leu
1               5

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Gln Trp Cys Ser Arg Arg Trp Cys Thr
1               5

<210> SEQ ID NO 574
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Asn Ala Cys Glu Ser Ala Ile Cys Gly
1               5

<210> SEQ ID NO 575
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Phe Pro Cys Glu Gly Lys Lys Cys Leu
1               5

<210> SEQ ID NO 576
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Ala Gly Cys Ile Asn Gly Leu Cys Gly
1               5

<210> SEQ ID NO 577

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Lys Gly Cys Gly Thr Arg Gln Cys Trp
1               5

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Lys Arg Cys Ser Ser Ser Leu Cys Ala
1               5

<210> SEQ ID NO 579
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Leu Asp Cys Leu Ser Glu Leu Cys Ser
1               5

<210> SEQ ID NO 580
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Ile Tyr Cys Pro Gly Gln Glu Cys Glu
1               5

<210> SEQ ID NO 581
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Glu Asp Cys Thr Ser Arg Phe Cys Ser
1               5

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Arg Trp Cys Arg Glu Lys Ser Cys Trp
```

-continued

```
1               5

<210> SEQ ID NO 583
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Cys Asn Lys Thr Asp Gly Asp Glu Gly Val Thr Cys
1               5                   10

<210> SEQ ID NO 584
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Cys Pro Leu Cys Asn Gly Arg Cys Ala Leu
1               5                   10

<210> SEQ ID NO 585
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Cys Glu Gln Cys Asn Gly Arg Cys Gly Gln
1               5                   10

<210> SEQ ID NO 586
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Cys Val Thr Cys Asn Gly Arg Cys Arg Val
1               5                   10

<210> SEQ ID NO 587
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Cys Glu Thr Cys Asn Gly Arg Cys Val Gly
1               5                   10

<210> SEQ ID NO 588
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 588

Cys Ser Cys Cys Asn Gly Arg Cys Gly Asp
1               5                   10

<210> SEQ ID NO 589
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Cys Lys Ser Cys Asn Gly Arg Cys Leu Ala
1               5                   10

<210> SEQ ID NO 590
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Cys Arg Thr Cys Asn Gly Arg Cys Gln Val
1               5                   10

<210> SEQ ID NO 591
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Cys Ala Ser Asn Asn Gly Arg Val Val Leu
1               5                   10

<210> SEQ ID NO 592
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Cys Ser Lys Cys Asn Gly Arg Cys Gly His
1               5                   10

<210> SEQ ID NO 593
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Cys Gly Glu Cys Asn Gly Arg Cys Val Glu
1               5                   10

<210> SEQ ID NO 594
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 594

Cys Glu Val Cys Asn Gly Arg Cys Ala Leu
1               5                   10

<210> SEQ ID NO 595
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

His His Thr Arg Phe Val Ser
1               5

<210> SEQ ID NO 596
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Trp Arg Val Leu Ala Ala Phe
1               5

<210> SEQ ID NO 597
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Ser Pro Gly Ser Trp Thr Trp
1               5

<210> SEQ ID NO 598
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Ile Lys Ala Arg Ala Ser Pro
1               5

<210> SEQ ID NO 599
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Leu Trp Ala Glu Met Thr Gly
1               5

<210> SEQ ID NO 600
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Ser Lys Ser Ser Gly Val Ser
1               5

<210> SEQ ID NO 601
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Val Val Asp Arg Phe Pro Asp
1               5

<210> SEQ ID NO 602
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Ile Met Tyr Pro Gly Trp Leu
1               5

<210> SEQ ID NO 603
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Cys Gln Leu Ala Ala Val Cys
1               5

<210> SEQ ID NO 604
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Cys Gly Leu Ser Asp Ser Cys
1               5

<210> SEQ ID NO 605
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Cys Glu Leu Ser Leu Ile Ser Lys Cys
1               5

<210> SEQ ID NO 606
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Cys Tyr Val Glu Leu His Cys
1               5

<210> SEQ ID NO 607
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Cys Tyr Ser Tyr Phe Leu Ala Cys
1               5

<210> SEQ ID NO 608
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Cys Asp Asp Ser Trp Lys Cys
1               5

<210> SEQ ID NO 609
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Cys Lys Ala Leu Ser Gln Ala Cys
1               5

<210> SEQ ID NO 610
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Val Pro Cys Arg Phe Lys Gln Cys Trp
1               5

<210> SEQ ID NO 611
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 611

Cys Met Glu Met Gly Val Lys Cys
1               5

<210> SEQ ID NO 612
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Cys Gly Thr Arg Val Asp His Cys
1               5

<210> SEQ ID NO 613
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Cys Tyr Leu Gly Val Ser Asn Cys
1               5

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Leu Val Cys Leu Pro Pro Ser Cys Glu
1               5

<210> SEQ ID NO 615
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Ile Ser Cys Ala Val Asp Ala Cys Leu
1               5

<210> SEQ ID NO 616
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Arg Ser Cys Ile Lys His Gln Cys Pro
1               5

<210> SEQ ID NO 617
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Gly Ile Cys Lys Asp Leu Trp Cys Gln
1               5

<210> SEQ ID NO 618
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Asn Arg Cys Arg Gly Val Ser Cys Thr
1               5

<210> SEQ ID NO 619
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Phe Gly Cys Val Met Ala Ser Cys Arg
1               5

<210> SEQ ID NO 620
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Asp Thr Cys Arg Ala Leu Arg Cys Asn
1               5

<210> SEQ ID NO 621
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Tyr Arg Cys Ile Ala Arg Glu Cys Glu
1               5

<210> SEQ ID NO 622
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Gln Ala Cys Pro Met Leu Leu Cys Met
```

```
1               5
```

<210> SEQ ID NO 623
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

```
His Thr Cys Leu Val Ala Leu Cys Ala
1               5
```

<210> SEQ ID NO 624
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

```
Arg Lys Cys Glu Val Pro Gly Cys Gln
1               5
```

<210> SEQ ID NO 625
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

```
Glu Ile Cys Val Asp Gly Leu Cys Val
1               5
```

<210> SEQ ID NO 626
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

```
Arg Pro Cys Gly Asp Gln Ala Cys Glu
1               5
```

<210> SEQ ID NO 627
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

```
Cys Glu Met Cys Asn Gly Arg Cys Met Gly
1               5                   10
```

<210> SEQ ID NO 628
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Cys Gly Val Cys Asn Gly Arg Cys Gly Leu
1               5                   10

<210> SEQ ID NO 629
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Cys Val Leu Cys Asn Gly Arg Cys Trp Ser
1               5                   10

<210> SEQ ID NO 630
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Cys Arg Thr Cys Asn Gly Arg Cys Leu Glu
1               5                   10

<210> SEQ ID NO 631
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Cys Arg Asp Leu Asn Gly Arg Lys Val Met
1               5                   10

<210> SEQ ID NO 632
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Cys Pro Leu Cys Asn Gly Arg Cys Ala Arg
1               5                   10

<210> SEQ ID NO 633
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Cys Gln Ser Cys Asn Gly Arg Cys Val Arg
1               5                   10

<210> SEQ ID NO 634
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 634

Cys Arg Cys Cys Asn Gly Arg Cys Ser Pro
1               5                   10

<210> SEQ ID NO 635
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Cys Trp Leu Cys Asn Gly Arg Cys Gly Arg
1               5                   10

<210> SEQ ID NO 636
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Cys Ile Arg Cys Asn Gly Arg Cys Ser Val
1               5                   10

<210> SEQ ID NO 637
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Cys Leu Ser Cys Asn Gly Arg Cys Pro Ser
1               5                   10

<210> SEQ ID NO 638
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Gly Arg Ser Gln Met Gln Ile
1               5

<210> SEQ ID NO 639
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Val Ala Ser Val Ser Val Ala
1               5
```

<210> SEQ ID NO 640
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Ile Phe Ser Gly Ser Arg Glu
1               5

<210> SEQ ID NO 641
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Gly Arg Trp Tyr Lys Trp Ala
1               5

<210> SEQ ID NO 642
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Ala Leu Val Gly Leu Met Arg
1               5

<210> SEQ ID NO 643
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Asp Thr Leu Arg Leu Arg Ile
1               5

<210> SEQ ID NO 644
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Val Trp Arg Thr Gly His Leu
1               5

<210> SEQ ID NO 645
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

```
Gly Leu Pro Val Lys Trp Ser
1               5

<210> SEQ ID NO 646
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Cys Val Arg Ile Arg Pro Cys
1               5

<210> SEQ ID NO 647
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Cys Val Ser Gly Pro Arg Cys
1               5

<210> SEQ ID NO 648
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Cys Tyr Thr Ala Asp Pro Cys
1               5

<210> SEQ ID NO 649
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Cys Leu Val Val His Glu Ala Ala Cys
1               5

<210> SEQ ID NO 650
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Cys Phe Trp Pro Asn Arg Cys
1               5

<210> SEQ ID NO 651
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 651

Cys Arg Leu Gly Ile Ala Cys
1               5

<210> SEQ ID NO 652
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Cys Tyr Pro Ala Asp Pro Cys
1               5

<210> SEQ ID NO 653
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Cys Gly Glu Thr Met Arg Cys
1               5

<210> SEQ ID NO 654
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Ser Trp Cys Gln Phe Glu Lys Cys Leu
1               5

<210> SEQ ID NO 655
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Cys Arg Glu Ser Leu Lys Asn Cys
1               5

<210> SEQ ID NO 656
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Cys Asn Asn Val Gly Ser Tyr Cys
1               5

<210> SEQ ID NO 657

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Cys Ala Met Val Ser Met Glu Asp
1               5

<210> SEQ ID NO 658
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Cys Ile Arg Ser Ala Val Ser Cys
1               5

<210> SEQ ID NO 659
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Phe Tyr Cys Pro Gly Val Gly Cys Arg
1               5

<210> SEQ ID NO 660
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Pro Arg Cys Glu Ser Gln Leu Cys Pro
1               5

<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Met Phe Cys Arg Met Arg Ser Cys Asp
1               5

<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Ala Pro Cys Gly Leu Leu Ala Cys Ile
```

-continued

```
1               5

<210> SEQ ID NO 663
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Ala Asp Cys Arg Gln Lys Pro Cys Leu
1               5

<210> SEQ ID NO 664
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Arg Ser Cys Ala Glu Pro Trp Cys Tyr
1               5

<210> SEQ ID NO 665
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Gly Arg Cys Val Asp Gly Gly Cys Thr
1               5

<210> SEQ ID NO 666
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Ile Cys Leu Leu Ala His Cys Ala
1               5

<210> SEQ ID NO 667
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Ala Gly Cys Arg Val Glu Ser Cys
1               5

<210> SEQ ID NO 668
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 668

Arg Leu Cys Ser Leu Tyr Gly Cys Val
1               5

<210> SEQ ID NO 669
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Leu Glu Cys Val Val Asp Ser Cys Arg
1               5

<210> SEQ ID NO 670
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Phe Arg Cys Leu Glu Arg Val Cys Thr
1               5

<210> SEQ ID NO 671
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Cys Asn Gly Arg Cys Val Ser Gly Cys Ala Gly Arg Cys
1               5                   10

<210> SEQ ID NO 672
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Ile Trp Ser Gly Tyr Gly Val Tyr Trp
1               5

<210> SEQ ID NO 673
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Trp Glu Ser Leu Tyr Phe Pro Arg Glu
1               5

<210> SEQ ID NO 674
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 674

Cys Gly Leu Met Cys Gln Gly Ala Cys Phe Asp Val Cys
1               5                   10

<210> SEQ ID NO 675
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Cys Pro Arg Gly Cys Leu Ala Val Cys Val Ser Gln Cys
1               5                   10

<210> SEQ ID NO 676
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Arg Leu Cys Arg Ile Val Val Ile Arg Val Cys Arg
1               5                   10

<210> SEQ ID NO 677
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 677

Tyr Val Pro Leu Pro Asn Val Pro Gln Pro Gly Arg Arg Pro Phe Pro
1               5                   10                  15

Thr Phe Pro Gly Gln Gly Pro Phe Asn Pro Lys Ile Lys Trp Pro Gln
            20                  25                  30

Gly Tyr

<210> SEQ ID NO 678
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 678

Val Phe Ile Asp Ile Leu Asp Lys Val Glu Asn Ala Ile His Asn Ala
1               5                   10                  15

Ala Gln Val Gly Ile Gly Phe Ala Lys Pro Phe Glu Lys Leu Ile Asn
            20                  25                  30

Pro Lys

<210> SEQ ID NO 679
<211> LENGTH: 18
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 679

Gly Asn Asn Arg Pro Val Tyr Ile Pro Gln Pro Arg Pro Pro His Pro
1               5                   10                  15

Arg Ile

<210> SEQ ID NO 680
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

Gly Asn Asn Arg Pro Val Tyr Ile Pro Gln Pro Arg Pro Pro His Pro
1               5                   10                  15

Arg Leu

<210> SEQ ID NO 681
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Gly Asn Asn Arg Pro Ile Tyr Ile Pro Gln Pro Arg Pro Pro His Pro
1               5                   10                  15

Arg Leu

<210> SEQ ID NO 682
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 682

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
                20                  25                  30

Pro Pro Phe Arg Pro Pro Leu Arg Phe Pro
                35                  40

<210> SEQ ID NO 683
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 683

Arg Arg Ile Arg Pro Arg Pro Pro Arg Leu Pro Arg Pro Arg Pro Arg
1               5                   10                  15

Pro Leu Pro Phe Pro Arg Pro Gly Pro Arg Pro Ile Pro Arg Pro Leu
                20                  25                  30

Pro Phe Pro Arg Pro Gly Pro Arg Pro Ile Pro Arg Pro Leu Pro Phe
            35                  40                  45

Phe Arg Pro Gly Pro Arg Pro Ile Pro Arg Pro
    50                  55

<210> SEQ ID NO 684
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Pro Arg Pro Ile Pro Arg Pro Leu Pro Phe Phe Arg Pro Gly Pro Arg
1               5                   10                  15

Pro Ile Pro Arg
            20

<210> SEQ ID NO 685
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 685

Trp Asn Pro Phe Lys Glu Leu Glu Arg Ala Gly Gln Arg Val Arg Asp
1               5                   10                  15

Ala Val Ile Ser Ala Ala Pro Ala Val Ala Thr Val Gly Gln Ala Ala
            20                  25                  30

Leu Ala Arg Gly
        35

<210> SEQ ID NO 686
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 686

Trp Asn Pro Phe Lys Glu Leu Glu Arg Ala Gly Gln Arg Val Arg Asp
1               5                   10                  15

Ala Ile Ile Ser Ala Gly Pro Ala Val Ala Thr Val Gly Gln Ala Ala
            20                  25                  30

Ala Ile Ala
        35

<210> SEQ ID NO 687
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 687

Trp Asn Pro Phe Lys Glu Leu Glu Arg Ala Gly Gln Arg Val Arg Asp
1               5                   10                  15

Ala Ile Ile Ser Ala Ala Pro Ala Val Ala Thr Val Gly Gln Ala Ala
            20                  25                  30

Ala Ile Ala Arg Gly
        35

<210> SEQ ID NO 688
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 688

Trp Asn Pro Phe Lys Glu Leu Glu Arg Ala Gly Gln Arg Val Arg Asp
1               5                   10                  15

Ala Val Ile Ser Ala Ala Pro Ala Val Ala Thr Val Gly Gln Ala Ala
            20                  25                  30

Ala Ile Ala Arg Gly Gly
        35

<210> SEQ ID NO 689
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Gly Ile Gly Ala Leu Ser Ala Lys Gly Ala Leu Lys Gly Leu Ala Lys
1               5                   10                  15

Gly Leu Ala Glx His Phe Ala Asn
            20

<210> SEQ ID NO 690
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

Gly Ile Gly Ala Ser Ile Leu Ser Ala Gly Lys Ser Ala Leu Lys Gly
1               5                   10                  15

Leu Ala Lys Gly Leu Ala Glu His Phe Ala Asn
            20                  25

<210> SEQ ID NO 691
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Gly Ile Gly Ser Ala Ile Leu Ser Ala Gly Lys Ser Ala Leu Lys Gly
1               5                   10                  15

Leu Ala Lys Gly Leu Ala Glu His Phe Ala Asn
            20                  25

<210> SEQ ID NO 692
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 692

Ile Lys Ile Thr Thr Met Leu Ala Lys Leu Gly Lys Val Leu Ala His
1               5                   10                  15
Val

<210> SEQ ID NO 693
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Ser Lys Ile Thr Asp Ile Leu Ala Lys Leu Gly Lys Val Leu Ala Ile
1               5                   10                  15
Ile Val

<210> SEQ ID NO 694
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Arg Pro Asp Phe Cys Leu Glu Pro Pro Tyr Thr Gly Pro Cys Lys Ala
1               5                   10                  15
Arg Ile Ile

<210> SEQ ID NO 695
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

Arg Tyr Phe Tyr Asn Ala Lys Ala Gly Leu Cys Gln Thr Phe Val Tyr
1               5                   10                  15
Gly

<210> SEQ ID NO 696
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Gly Cys Arg Ala Lys Arg Ile Asn Asn Phe Lys Ser Ala Glu Asp Cys
1               5                   10                  15
Met Arg Thr Cys Gly Gly Ala
            20

<210> SEQ ID NO 697
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 697

Phe Leu Pro Leu Leu Ala Gly Leu Ala Ala Asn Phe Leu Pro Lys Ile
1               5                   10                  15

Phe Cys Lys Ile Thr Arg Lys Cys
                20

<210> SEQ ID NO 698
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Gly Ile Met Asp Thr Leu Lys Asn Leu Ala Lys Thr Ala Gly Lys Gly
1               5                   10                  15

Ala Leu Gln Ser Leu Leu Asn Lys Ala Ser Cys Lys Leu Ser Gly Gln
                20                  25                  30

Cys

<210> SEQ ID NO 699
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 699

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
                20                  25                  30

Thr Gln Ile Ala Lys
        35

<210> SEQ ID NO 700
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
                20                  25                  30

Lys Ala Leu
        35

<210> SEQ ID NO 701
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 701

Gly Trp Ile Leu Lys Lys Leu Gly Lys Arg Ile Glu Arg Ile Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly
        35                  40

<210> SEQ ID NO 702
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Trp Asn Pro Phe Lys Glu Leu Glu Lys Val Gly Gln Arg Val Arg Asp
1               5                   10                  15

Ala Val Ile Ser Ala Gly Pro Ala Val Ala Thr Val Ala Gln Ala Thr
            20                  25                  30

Ala Leu Ala Lys
        35

<210> SEQ ID NO 703
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 704
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 704

Glx Phe Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
            20                  25                  30

Cys Arg Cys Tyr Ser
        35

<210> SEQ ID NO 705
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Phe Leu Pro Leu Ile Leu Arg Lys Ile Val Thr Ala Leu
1               5                   10

<210> SEQ ID NO 706
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706

Leu Arg Asp Leu Val Cys Tyr Cys Arg Ser Arg Gly Cys Lys Gly Arg
1               5                   10                  15

Glu Arg Met Asn Gly Thr Cys Arg Lys Gly His Leu Leu Tyr Thr Leu
            20                  25                  30

Cys Cys Arg
        35

<210> SEQ ID NO 707
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Leu Arg Asp Leu Val Cys Tyr Cys Arg Thr Arg Gly Cys Lys Arg Arg
1               5                   10                  15

Glu Arg Met Asn Gly Thr Cys Arg Lys Gly His Leu Met Tyr Thr Leu
            20                  25                  30

Cys Cys Arg
        35

<210> SEQ ID NO 708
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 708

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Thr Pro Leu Cys Cys
            20                  25                  30

Arg Arg

<210> SEQ ID NO 709
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 709

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 710
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 710

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 711
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 711

Arg Arg Cys Ile Cys Thr Thr Arg Thr Cys Arg Phe Pro Tyr Arg Arg
1               5                   10                  15

Leu Gly Thr Cys Leu Phe Gln Asn Arg Val Tyr Thr Phe Cys Cys
            20                  25                  30

<210> SEQ ID NO 712
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 712

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 713
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 714
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 714

```
Val Val Cys Ala Cys Arg Arg Ala Leu Cys Leu Pro Arg Glu Arg
1               5                   10                  15

Ala Gly Phe Cys Arg Ile Arg Gly Arg Ile His Pro Leu Cys Cys Arg
            20                  25                  30

Arg

<210> SEQ ID NO 715
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 715

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 716
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 716

Val Thr Cys Tyr Cys Arg Arg Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 717
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 717

Val Thr Cys Tyr Cys Arg Ser Thr Arg Cys Gly Phe Arg Glu Arg Leu
1               5                   10                  15

Ser Gly Ala Cys Gly Tyr Arg Gly Arg Ile Tyr Arg Leu Cys Cys Arg
            20                  25                  30

<210> SEQ ID NO 718
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 718

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35
```

<210> SEQ ID NO 719
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 719

Val Arg Asn His Val Thr Cys Arg Ile Asn Arg Gly Phe Cys Val Pro
1               5                   10                  15

Ile Arg Cys Pro Gly Arg Thr Arg Gln Ile Gly Thr Cys Phe Gly Pro
            20                  25                  30

Arg Ile Lys Cys Cys Arg Ser Trp
        35                  40

<210> SEQ ID NO 720
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 720

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
        35

<210> SEQ ID NO 721
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 721

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
        35                  40

<210> SEQ ID NO 722
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 722

Gly Phe Gly Cys Pro Leu Asp Gln Met Gln Cys His Arg His Cys Gln
1               5                   10                  15

Thr Ile Thr Gly Arg Ser Gly Gly Tyr Cys Ser Gly Pro Leu Lys Leu
            20                  25                  30

Thr Cys Thr Cys Tyr Arg
        35

<210> SEQ ID NO 723
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 723

Gly Phe Gly Cys Pro Leu Asn Gln Gly Ala Cys His Arg His Cys Arg
1               5                   10                  15

Ser Ile Arg Arg Arg Gly Gly Tyr Cys Ala Gly Phe Phe Lys Gln Thr
            20                  25                  30

Cys Thr Cys Tyr Arg Asn
        35

<210> SEQ ID NO 724
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 724

Ala Leu Trp Lys Thr Met Leu Lys Lys Leu Gly Thr Met Ala Leu His
1               5                   10                  15

Ala Gly Lys Ala Ala Leu Gly Ala Ala Asp Thr Ile Ser Gln Thr Gln
            20                  25                  30

<210> SEQ ID NO 725
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

Gly Lys Pro Arg Pro Tyr Ser Pro Arg Pro Thr Ser His Pro Arg Pro
1               5                   10                  15

Ile Arg Val

<210> SEQ ID NO 726
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 726

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Asp Ile Ala Gly Cys Lys Ile Lys Gly Glu Cys
        35                  40                  45

<210> SEQ ID NO 727
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 727

Ile Leu Pro Trp Lys Trp Pro Trp Trp Pro Trp Arg Arg
1               5                   10

<210> SEQ ID NO 728
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Phe Lys Cys Arg Arg Trp Gln Trp Arg Met Lys Lys Leu Gly Ala Pro
1               5                   10                  15

Ser Ile Thr Cys Val Arg Arg Ala Pro
            20                  25

<210> SEQ ID NO 729
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 730
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 730

Thr Ala Gly Pro Ala Ile Arg Ala Ser Val Lys Gln Cys Gln Lys Thr
1               5                   10                  15

Leu Lys Ala Thr Arg Leu Phe Thr Val Ser Cys Lys Gly Lys Asn Gly
            20                  25                  30

Cys Lys

<210> SEQ ID NO 731
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 731

Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30
```

```
Pro Gly Cys Val Thr Gly Ala Leu Gln Thr Cys Phe Leu Gln Thr Leu
        35                  40                  45

Thr Cys Asn Cys Lys Ile Ser Lys
    50                  55

<210> SEQ ID NO 732
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Lys Tyr Tyr Gly Asn Gly Val His Cys Thr Lys Ser Gly Cys Ser Val
1               5                   10                  15

Asn

<210> SEQ ID NO 733
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Trp Gly Glu Ala Phe Ser Ala Gly Val His Arg Leu Ala Asn Gly Gly
1               5                   10                  15

Asn Gly Phe Trp
            20

<210> SEQ ID NO 734
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Gly Ile Gly Lys Phe Leu His Ser Ala Gly Lys Phe Gly Lys Ala Phe
1               5                   10                  15

Val Gly Glu Ile Met Lys Ser
            20

<210> SEQ ID NO 735
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 736
<211> LENGTH: 21
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 736

Gly Met Ala Ser Lys Ala Gly Ala Ile Ala Gly Lys Ile Ala Lys Val
1               5                   10                  15

Ala Leu Lys Ala Leu
            20

<210> SEQ ID NO 737
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Gly Val Leu Ser Asn Val Ile Gly Tyr Leu Lys Lys Leu Gly Thr Gly
1               5                   10                  15

Ala Leu Asn Ala Val Leu Lys Gly
            20

<210> SEQ ID NO 738
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Gly Trp Ala Ser Lys Ile Gly Gln Thr Leu Gly Lys Ile Ala Lys Val
1               5                   10                  15

Gly Leu Lys Glu Leu Ile Gln Pro Lys
            20                  25

<210> SEQ ID NO 739
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Ile Asn Leu Lys Ala Leu Ala Ala Leu Ala Lys Lys Ile Leu
1               5                   10

<210> SEQ ID NO 740
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 741
<211> LENGTH: 40
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 741

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Gly Val Cys Val Cys Arg Asn
        35                  40

<210> SEQ ID NO 742
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 742

Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Arg
            20                  25                  30

Lys Gly Val Cys Val Arg Asn
        35

<210> SEQ ID NO 743
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Arg Arg Trp Cys Phe Arg Val Cys Tyr Arg Gly Phe Cys Tyr Arg Lys
1               5                   10                  15

Cys Arg

<210> SEQ ID NO 744
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Arg Arg Trp Cys Phe Arg Val Cys Tyr Lys Gly Phe Cys Tyr Arg Lys
1               5                   10                  15

Cys Arg

<210> SEQ ID NO 745
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Arg Gly Gly Arg Leu Cys Tyr Cys Arg Arg Arg Phe Cys Val Cys Val
1               5                   10                  15
```

Gly Arg

<210> SEQ ID NO 746
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Arg Gly Gly Arg Leu Cys Tyr Cys Arg Arg Phe Cys Ile Cys Val
1               5                   10                  15

<210> SEQ ID NO 747
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Arg Gly Gly Gly Leu Cys Tyr Cys Arg Arg Phe Cys Val Cys Val
1               5                   10                  15

Gly Arg

<210> SEQ ID NO 748
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 748

Val Thr Cys Asp Leu Leu Ser Phe Lys Gly Gln Val Asn Asp Ser Ala
1               5                   10                  15

Cys Ala Ala Asn Cys Leu Ser Leu Gly Lys Ala Gly Gly His Cys Glu
            20                  25                  30

Lys Gly Val Cys Ile Cys Arg Lys Thr Ser Phe Lys Asp Leu Trp Asp
        35                  40                  45

Lys Tyr Phe
    50

<210> SEQ ID NO 749
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 749

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

<210> SEQ ID NO 750
<211> LENGTH: 39
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 750

Gly Trp Leu Lys Lys Ile Gly Lys Lys Ile Glu Arg Val Gly Gln His
1               5                   10                  15

Thr Arg Asp Ala Thr Ile Gln Val Ile Gly Val Ala Gln Gln Ala Ala
            20                  25                  30

Asn Val Ala Ala Thr Ala Arg
        35

<210> SEQ ID NO 751
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 751

Ser Asp Glu Lys Ala Ser Pro Asp Lys His His Arg Phe Ser Leu Ser
1               5                   10                  15

Arg Tyr Ala Lys Leu Ala Asn Arg Leu Ala Asn Pro Lys Leu Leu Glu
            20                  25                  30

Thr Phe Leu Ser Lys Trp Ile Gly Asp Arg Gly Asn Arg Ser Val
        35                  40                  45

<210> SEQ ID NO 752
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Lys Trp Cys Phe Arg Val Cys Tyr Arg Gly Ile Cys Tyr Arg Arg Cys
1               5                   10                  15

Arg

<210> SEQ ID NO 753
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 753

Arg Trp Cys Phe Arg Val Cys Tyr Arg Gly Ile Cys Tyr Arg Lys Cys
1               5                   10                  15

Arg

<210> SEQ ID NO 754
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 754

Lys Ser Cys Cys Lys Asp Thr Leu Ala Arg Asn Cys Tyr Asn Thr Cys

```
                1               5                  10                 15
Arg Phe Ala Gly Gly Ser Arg Pro Val Cys Ala Gly Ala Cys Arg Cys
                    20                  25                 30

Lys Ile Ile Gly Pro Lys Cys Pro Ser Asp Tyr Pro Lys
        35                  40                 45

<210> SEQ ID NO 755
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Gly Gly Lys Pro Asp Leu Arg Pro Cys Ile Ile Pro Pro Cys His Tyr
1               5                   10                  15

Ile Pro Arg Pro Lys Pro Arg
            20

<210> SEQ ID NO 756
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 756

Val Lys Asp Gly Tyr Ile Val Asp Asp Val Asn Cys Thr Tyr Phe Cys
1               5                   10                  15

Gly Arg Asn Ala Tyr Cys Asn Glu Glu Cys Thr Lys Leu Lys Gly Glu
            20                  25                  30

Ser Gly Tyr Cys Gln Trp Ala Ser Pro Tyr Gly Asn Ala Cys Tyr Cys
        35                  40                  45

Lys Leu Pro Asp His Val Arg Thr Lys Gly Pro Gly Arg Cys His
    50                  55                  60

<210> SEQ ID NO 757
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Ala Ala Arg Gly Asp Tyr
1               5

<210> SEQ ID NO 758
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Asp Gly Arg Lys Phe
1               5
```

DUAL FUNCTION POLYMER MICELLES

This application is a national phase of International Application No. PCT/US2005/019308 filed Jun. 2, 2005 and published in the English language, and claims priority to U.S. Ser. No. 60/577,142 filed Jun. 6, 2004.

This work was supported by Federal Grant Nos. NIH-R01-CA-90696 and CA-93993. The U.S. government may have certain rights in this invention.

SEQUENCE LISTING

The instant application contains a Sequence Listing which has been submitted in ASCII format via EFS-Web and is hereby incorporated by reference in its entirety. Said ASCII copy, created on Oct. 29, 2010, is named CASEP887WOUS Substitute Sequence Listing.txt and is 189,054 bytes in size.

FIELD OF INVENTION

This invention relates to functionalized micelles suitable for use as delivery vehicles.

BACKGROUND OF THE INVENTION

An important objective in cancer therapy is to selectively deliver therapeutic agents to the tumor tissue. Low water solubility, rapid phagocytic and renal clearance, and systemic toxicity represent three major barriers that limit the therapeutic use of many hydrophobic anti-tumor agents such as doxorubicin (DOX) and paclitaxel. To overcome these limitations, various drug delivery systems, among which polymeric micelles have emerged as one important class, have been developed for delivering various drugs with varying degrees of in vitro and in vivo success. The hydrophobic core of the micelles is a carrier compartment that accommodates anti-tumor drugs, and the outside surface of the micelle consists of a brush-like protective corona that stabilizes the nanoparticles in aqueous solution.

Polymeric micelles in drug delivery applications are typically characterized by high drug-loading capacity, biodegradability, long blood circulation, and controllable drug release profiles. Polymeric micelles from amphiphilic block copolymers are supramolecular core-shell-type assemblies of tens of nanometers in diameter, which can mimic naturally occurring biological transport systems such as lipoproteins and viruses. Recently, polymeric micelles as carriers of hydrophobic drugs have drawn increasing interest, due to their various advantages in drug delivery applications. First, polymeric micelles are highly stable in aqueous solution because of their intrinsic low critical micelle concentration (cmc), which prevents the drug-entrapped micelles from dissociation upon dilution in the blood stream after intravenous injection. Furthermore, the nanoscale size of polymeric micelles can facilitate their extravasations at tumor sites while avoiding renal clearance and non-specific reticuloendothelial (RES) uptake. The micelle cores are usually constructed with biodegradable polymers such as aliphatic polyesters and polypeptide, and water-soluble poly(ethylene glycol) is most frequently used to build the micelle corona because it can effectively stabilize the nanoparticles in blood compartments and reduce the uptake at the reticuloendothelial sites (e.g. liver and spleen). By encapsulating drugs within the micelles, solubility limits for hydrophobic drugs can be exceeded.

Antitumor drugs, such as doxorubicin (DOX) and paclitaxel, are widely used in cancer chemotherapy. Besides their low water solubility, major drawbacks of these drugs are the acute toxicity to normal tissue and inherent multi-drug resistance effect. To reduce the acute toxicity of the free drugs and improve their therapeutic efficacy, various liposome and polymeric micelle systems were designed as delivery vehicles. Hydrophobic drugs can be incorporated into the micelle inner core by both chemical conjugation and physical entrapment, depending on the chemical structure of drugs. For instances, paclitaxel was encapsulated into micelle cores usually by physical entrapment driven by hydrophobic interactions between the drug and the hydrophobic components of polymers. In contrast, doxorubicin can also be chemically bound to the core of polymeric micelles through amidation of doxorubicin amino groups, yielding high loading content. By this way, an efficient doxorubicin delivery system based on doxorubicin-conjugated poly(ethylene glycol)-poly(aspartic acid) block copolymer (PEG-PAsp-(DOX)) has been developed. The conjugation with DOX converted the hydrophilic poly(aspartic acid) into hydrophobic blocks that formed the hydrophobic micelle core and physically entrapped free DOX as well. Recently, DOX conjugation to the micelle cores through an acid-cleavable linkage, such as a hydrazone bond, was reported to be an effective way to enhance the bioavailability of the chemically bound DOX. The hydrazone linkage was cleaved in the endosomes/lysosomes (pH around 5) to yield free DOX molecules which then functioned as the physically entrapped DOX. Compared to the chemical conjugation strategy, physical entrapment of drugs in the micelle cores may be advantageous in terms of easy polymer preparation, simple micelle fabrication, and enhanced drug bioavailability. Although several micellar systems based on non-ionic amphiphilic block polymers such as PEO-PPO-PEO and PEG-b-PBLA have been reported, physically entrapped DOX delivery with polymeric micelles based on the well-known block copolymers of poly(ethylene glycol) and biodegradable polyesters is still very limited. Research on micelles has been greatly advanced; however, the ability to achieve high targeting efficiency at the tumor site and associated cells remains a significant challenge for the development of micelle-mediated drug delivery systems.

SUMMARY OF THE INVENTION

The invention relates in part to micelles that are elaborated with functionality that enables the micelles to selectively target tumor tissue in the delivery of hydrophobic agents. Thus, one aspect of the invention is the elaboration of the outer surface (corona) of the micelle with various protein sequences that selectively bind to certain types of tissue. These functionalized micelles may further comprise a hydrophobic chemotherapeutic agent in the core of the micellar structure, such as doxorubicin (DOX) or paclitaxel. Alternatively or additionally, these micelles may further comprise a hydrophobic MRI imaging agent in the core of the micellar structure, such as superparamagnetic iron oxide (SPIO).

Another aspect of the invention is the incorporation of radioactive moieties onto the surface of the micellar structure to facilitate single photon emission computed tomography (SPECT), which provides information about the availability of radioisotopes with high sensitivity and the capability to simultaneously monitor multiple probes with different emission wavelengths. This technique may be useful in measuring the in vivo pharmacokinetics and tumor targeting efficiency of drug loaded micelles.

BRIEF DESCRIPTION OF THE FIGURES

FIG. 5a shows the percentage of micelle uptake in SLK tumor endothelial cells measured by flow cytometry as a function of cRGD density on the micelle surface.

FIG. 5b shows confocal laser scanning microscopy images of SLK cells treated with 0% cRGD after incubation for 2 h.

FIG. 5c shows confocal laser scanning microscopy images of SLK cells treated with 16% cRGD after incubation for 2 h.

FIG. 8a shows a transmission electron micrograph of a typical micelle containing numerous individual SPIO particles.

FIG. 8b shows a T$_2$-weighted MRI image of a control mouse tumor.

FIG. 8c shows a T$_2$-weighted MRI image of a tumor 72 hours after micelle administration.

DETAILED DESCRIPTION OF THE INVENTION

Figure 1:
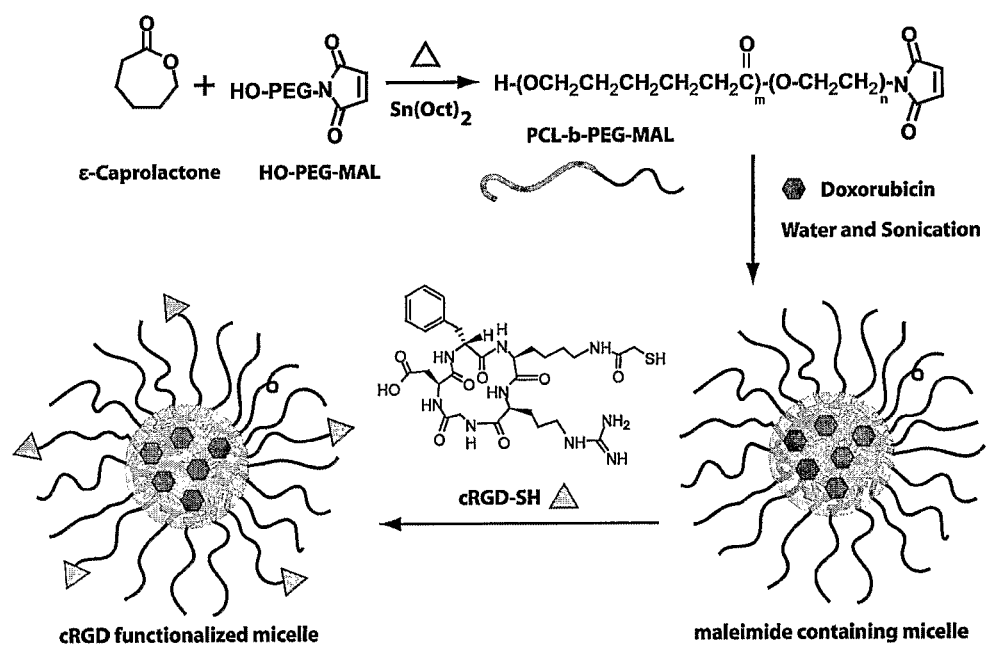
FIG. 1 shows the preparation of cRGD-DOX-micelles.

One strategy to achieve cancer-targeted drug delivery is the utilization of unique molecular markers that are specifically overexpressed in the cancerous tissues. It is well known that tumor endothelial cells show increased expression of several cell surface molecules that potentiate cell invasion and proliferation during tumor vascular remodeling and angiogenesis. Thus, one aspect of the invention is the attachment of moieties to the corona of a polymeric micellar structure that can effectively bind to such molecular markers.

In certain embodiments, the micelles are formed from amphiphilic block copolymers. In preferred embodiments, the polymer is selected from poly-γ-benzyl-L-glutamate-polyethylene oxide (PBLG-PEO), poly(ethylene oxide)-poly(propylene oxide) (PEO-PPO-PEO), poly(ethylene glycol)-poly(β-benzyl-L-aspartate) (PEG-b-PBLA), and poly(ε-caprolactone)-poly(ethylene glycol) (PCL-PEG). In most preferred embodiments, the polymer is PCL-PEG.

Micelles may be prepared by adding the copolymer and optionally any additional hydrophobic agent(s) to a hydrophobic solvent in which they are soluble (an organic solvent), the resulting solution being added to water under conditions of vigorous agitation, for example, by ultrasonication, shaking, or other suitable agitation as is well understood in the art. The organic solvent may then be removed by slow evaporation to promote the formation of micelles. The residual organic solvent may then be completely removed to provide the desired micelles in an aqueous medium.

In preferred such embodiments, micelles may contain a hydrophobic agent in the core, wherein a "hydrophobic agent" is an agent that is poorly soluble in water, such as an agent that is more soluble in octanol than it is soluble in water. Preferably, the hydrophobic agent is a chemotherapeutic drug. In certain such embodiments, the chemotherapeutic drug is selected from aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine. In more preferred such embodiments, the chemotherapeutic drug is selected from paclitaxel and doxorubicin.

In certain embodiments, the micelles are functionalized with a targeting moiety. The term "targeting moiety" refers to any molecular structure which assists the micelle in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins can serve as targeting moieties. A number of suitable targeting moieties are disclosed in U.S. Patent Application 2003-0049203, which is incorporated herein in its entirety.

Since tumor endothelial cells show increased expression of several cell surface molecules, the attachment of moieties to the corona of a polymeric micellar structure that can effectively bind to such molecular markers may serve as a way to target such tumor tissue. One molecular marker known to be overexpressed in cancerous tissue is $\alpha_v\beta_3$ integrin, which plays a key role in endothelial cell survival during angiogenesis (Griffioen A. W., Molema G. (2000) *Pharmacol. Rev.* 52 237-268). The $\alpha_v\beta_3$ integrin was found to be unregulated in these cells and can induce cell internalization (Brooks P. C. et al. (1994) *Cell.* 79, 1157-1164). In preferred embodiments, an $\alpha_v\beta_3$ ligand is bound to the corona of micelles. In certain embodiments, c(Arg-Gly-Asp-D-Phe-Lys) (c-RGD) is bound to the corona of micelles.

Examples of other suitable targeting moieties include but are not limited to lipoproteins, glycoproteins, asialoglycoproteins, transferrin, toxins, carbohydrates, cell surface receptor ligands, antibodies, and homing peptides. Synthetic homing peptides with the desired levels of affinity and/or selectivity for specific organs or tissues may be employed as targeting moieties, for example as disclosed in U.S. Pat. Nos. 6,576,239, 6,306,365, 6,303,573, 6,296,832, 6,232,287, 6,180,084, 6,174,687, 6,068,829, and 5,622,699, U.S. patent applications 2001/0046498, 2002/0041898, 2003/0008819, and 2003/0077826, and PCT application PCT/GB02/04017 (WO 03/020751), all of which are incorporated herein by reference.

Methods for identifying and using these and other tissue-homing peptides are known in the art, see for example W. Arap et al., *Science* 279:377-380 (1998); R. Pasqualini, and E. Ruoslahti, *Nature* 380:364-366 (1996); D. Rajotte et al., *J. Clin. Invest.* 102:430-437 (1998); P. Laakkonen et al., *Nature Medicine* 8(7):751-755 (2002); and K. Essler, E. Ruoslahti, *Proc. Natl. Acad. Sci. U.S.A.* 99(4):2252-2257 (2002), all of which are hereby incorporated herein by reference in their entirety. Suitable tissue-specific homing peptides include, but are not limited to, the sequences in Table 1

TABLE 1

| | SEQ ID NO: | | SEQ ID NO: |
|---|---|---|---|
| Brain: | | | |
| CLSSRLDAC | 1 | CVLRGGRC | 2 |
| CNSRLQLRC | 3 | CGVRLGC | 4 |
| CKDWGRIC | 5 | CLDWGRIC | 6 |
| CTRITESC | 7 | CETLPAC | 8 |
| CRTGTLFC | 9 | CGRSLDAC | 10 |
| CRHWFDVVC | 11 | CANAQSHC | 12 |
| CGNPSYRC | 13 | WRCVLREGPAGGCAWFNRHRL | 14 |
| YPCGGEAVAGVSSVRTMCSE | 15 | LNCDYQGTNPATSVSVPCTV | 16 |
| CNSRLHLRCCENWWGDVC | 17 | WRCVLREGPAGGGAWFNRHRL | 18 |
| Kidney: | | | |
| CLPVASC | 19 | CGAREMC | 20 |
| CKGRSSAC | 21 | CWARAQGC | 22 |
| CLGRSSVC | 23 | CTSPGGSC | 24 |
| CMGRWRLC | 25 | CVGECGGC | 26 |
| CVAWLNC | 27 | CRRFQDC | 28 |
| CLMGVHC | 29 | CKLLSGVC | 30 |
| CFVGHDLC | 31 | CRCLNVC | 32 |
| CKLMGEC | 33 | | |
| Heart: | | | |
| GGGVFWQ | 34 | HGRVRPH | 35 |
| VVLVTSS | 36 | CLHRGNSC | 37 |
| CRSWNKADNRSC | 38 | | |
| Gut: | | | |
| YAGFFLV | 39 | RSGARSS | 40 |
| CVESTVA | 41 | SRRQPLS | 42 |
| SKVWLLL | 43 | QVRRVPE | 44 |
| YSGKWGW | 45 | MVQSVG | 46 |
| LRAVGRA | 47 | MSPQLAT | 48 |
| GAVLPGE | 49 | WIEEAER | 50 |

TABLE 1-continued

| | SEQ ID NO: | | SEQ ID NO: |
|---|---|---|---|
| LVSEQLR | 51 | RGDRPPY | 52 |
| VRRGSPQ | 53 | RVRGPER | 54 |
| GISAVLS | 55 | GGRGSWE | 56 |
| GVSASDW | 57 | FRVRGSP | 58 |
| SRLSGGT | 59 | WELVARS | 60 |
| MRRDEQR | 61 | GCRCWA | 62 |
| LSPPYMW | 63 | LCTAMTE | 64 |
| Integrins: | | | |
| CRGDC | 65 | CRGDCL | 66 |
| CRGDCA | 67 | NGRAHA | 68 |
| DGRAHA | 69 | RCDVVV | 70 |
| SLIDIP | 71 | TIRSVD | 72 |
| KRGD | 73 | RRGD | 74 |
| RGDL | 75 | | |
| RGD-binding determinants: | | | |
| CSFGRGDIRNC | 76 | CSFGRTDQRIC | 77 |
| CSFGKGDNRIC | 78 | CSFGRNDSRNC | 79 |
| CSFGRVDDRNC | 80 | CSFGRADRRNC | 81 |
| CSFGRSVDRNC | 82 | CSFGKRDMRNC | 83 |
| CSFGRWDARNC | 84 | CSFGRQDVRNC | 85 |
| CSFGRDDGRNC | 86 | | |
| Angiogenic tumor endothelium: | | | |
| CDCRGDCFC | 87 | CNGRCVSGCAGRC | 88 |
| Ovary: | | | |
| EVRSRLS | 89 | RVGLVAR | 90 |
| AVKDYFR | 91 | GVRTSIW | 92 |
| RPVGMRK | 93 | RVRLVNL | 94 |
| FFAAVRS | 95 | KLVNSSW | 96 |
| LCERVWR | 97 | FGSQAFV | 98 |
| WLERPEY | 99 | GGDVMWR | 100 |
| VRARLMS | 101 | TLRESGP | 102 |
| Uterus: | | | |
| GLSGGRS | 103 | SWCEPGWCR | 104 |
| Prostate: | | | |
| EVQSAKW | 105 | KRVYVLG | 106 |
| GRLSVQV | 107 | WKPASLS | 108 |
| FAVRVVG | 109 | LVRPLEG | 110 |

TABLE 1-continued

| | SEQ ID NO: | | SEQ ID NO: | | SEQ ID NO: | | SEQ ID NO: |
|---|---|---|---|---|---|---|---|
| GFYRMLG | 111 | EGRPMVY | 112 | CADYDLALGLMC | 185 | CPKARPAPQYKC | 186 |
| GSRSLGA | 113 | RVWQGDV | 114 | CSSHQGGFQHGC | 187 | CQETRTEGRKKC | 188 |
| GDBLLA | 115 | FVWLVGS | 116 | CRPWHNQAHTEC | 189 | CSFGTHDTEPHC | 190 |
| GSEPMFR | 117 | VSFLEYR | 118 | CSEAASRMIGVC | 191 | CWEEHPSIKWWC | 192 |
| WHQPL | 119 | SMSIARL | 120 | CWDADQIEGIKC | 193 | CVDSQSMKGLVC | 194 |
| RGRWLAL | 121 | QVEEFPC | 122 | CRLQTMGQGQSC | 197 | CRPAQRDAGTSC | 196 |
| LWLSGNW | 123 | GPMLSVM | 124 | CGGRDRGTYGPC | 199 | GGEVASNERIQC | 198 |
| WTFLERL | 125 | VLPGGQW | 126 | CNSKSSAELEKC | 201 | CVLNFKNQARDC | 200 |
| REVKES | 127 | RTPAAVM | 128 | CRGKPLANFEDC | 203 | CEGHSMRGYGLC | 202 |
| GEWLGEC | 129 | PNPLMPL | 130 | CRDRGDRMKSLC | 205 | CDNTCTYGVDDC | 204 |
| SLWYLGA | 131 | YVGGWEL | 132 | CSAHSQEMNVNC | 207 | CGAACGVGCRGRC | 206 |
| Lung: | | | | CGFECVRQCPERC | 209 | CLVGCRLSCGGEC | 208 |
| CGFECVRQCPERC | 133 | CTLRDRNC | 134 | CRSGCVEGCGGRC | 211 | CIARCGGACGRHC | 210 |
| CIKGNVNC | 135 | CRHESSSC | 136 | CGGECGWECEVSC | 213 | CGVGCPGLCGGAC | 212 |
| CLYIDRRC | 137 | CYSLGADC | 138 | CKWLCLLLCAVAC | 215 | CSEGCGPVCWPEC | 214 |
| CSKLMMTC | 139 | CGFELETC | 140 | CGAACGVGCGGRC | 217 | CSGSCRRGCGIDC | 216 |
| CNSDVDLC | 141 | CVGNLSMC | 142 | CGASCALGCRAYC | 219 | CDTSCENNCQGPC | 218 |
| CEKKLLYC | 143 | CKGQRDFC | 144 | CSRQCRGACGQPC | 221 | CYWWCDGVCALQC | 220 |
| CTFRNASC | 145 | CNMGLTRC | 146 | CAGGGAVRCGGTC | 223 | CGGACGGVCTGGC | 222 |
| CHEGYLTC | 147 | CGTFGARC | 148 | CGRPCVGECRMGC | 225 | CLVGCEVGCSPAC | 224 |
| CIGEVEVC | 149 | CRISAHPC | 150 | CPRTCGAACASPC | 227 | CRGDCGIGCRRLC | 226 |
| CLRPYLNC | 151 | CSYPKILC | 152 | CCFTNFDCYLGC | | | |
| CMELSKQG | 153 | CSEPSGTC | 154 | Skin: | | | |
| CGNETLRC | 155 | CTLSNRFC | 156 | CYADCEGTCGMVC | 228 | CWNICPGGCRALC | 229 |
| CMGSEYWC | 157 | CLFSDENC | 158 | GPGCEEECQPAC | 230 | CKGTCVLGCSEEC | 231 |
| CAHQHIQC | 159 | CKGQGDWC | 160 | CSTLCGLRCMGTC | 232 | CMPRCGVNCKWAC | 233 |
| CAQNMLCC | 161 | CWRGDRKIC | 162 | CVGACDLKCTGGC | 234 | CVALCREACGEGC | 235 |
| CLAKENVVC | 163 | CIFREANVC | 164 | CSSGCSKNCLEMC | 236 | CGRPCRGGCAASC | 237 |
| CRTHGYQGC | 165 | CERVVGSSC | 166 | CQGGCGVSCPIFC | 238 | CAVRCDGSCVPEC | 239 |
| CKTNHMESC | 167 | CYEEKSQSC | 168 | CGFGCSGSCQMQC | 240 | CRVVCADGCRFIC | 241 |
| CKDSAMTIC | 169 | CTRSTNTGC | 170 | CTMGCTAGCAFAC | 242 | CEGKCGLTCECTC | 243 |
| CMSWDAVSC | 171 | CKWSRLHSC | 172 | CNQGCSGSCDVMC | 244 | CASGCSESCYVGC | 245 |
| CMSPQRSDC | 173 | CLHSPRSKC | 174 | CGGGCQWGCAGEC | 246 | CSVRCKSVCIGLC | 247 |
| CPQDIRRNC | 175 | CLYTKEQRC | 176 | CPSNCVALCTSGC | 248 | CVEGCSSGCGPGC | 249 |
| CQTRNFAQC | 177 | CTGHLSTDC | 178 | CRVVCADGCRLIC | 250 | CSTLCGLRCMGTC | 251 |
| CQDLNIMQC | 179 | TRRTNNPLT | 180 | CFTFCEYHCQLTC | 252 | | |
| CGYIDPNRISQC | 181 | CTVNEAYKTRMC | 182 | Retina: | | | |
| CRLRSYGTLSLC | 183 | CAGTCATGCNGVC | 184 | CRRIWYAVC | 253 | CSAYTTSPC | 254 |

TABLE 1-continued

| | SEQ ID NO: | | SEQ ID NO: |
|---|---|---|---|
| CSCFRDVCC | 255 | CTDKSWPC | 256 |
| CTDNRVGS | 257 | CTIADFPC | 258 |
| CTSDISWWDYKC | 259 | CTVDNELC | 260 |
| CVGDCIGSCWMFC | 261 | CVKFTYDC | 262 |
| CVSGHLNC | 263 | CYGESQQMC | 264 |
| CYTGETWTC | 265 | CAVSIPRC | 266 |
| CDCRGDCFC | 267 | CDSLCGGACAARC | 268 |
| CERSQSKGVHHC | 269 | CFKSTLLC | 270 |
| CFWHNRAC | 271 | CGDVCPSECPGWC | 272 |
| CGEFKVGC | 273 | CGLDCLGDCSGAC | 274 |
| CGPGYQAQCSLRC | 275 | CGSHCGQLCKSLC | 276 |
| CHMGCVSPCAYVC | 277 | CILSYDNPC | 278 |
| CISRPYFC | 279 | CKERLEYTRGVC | 280 |
| CKERPSNGLSAC | 281 | CKPFRTEC | 282 |
| CKSGCGVACRHMC | 283 | CLKPGGQEC | 284 |
| CMDSQSSC | 285 | CMNILSGC | 286 |
| CNIPVTTPIFGC | 287 | CNQRTNRESGNC | 288 |
| CNRKNSNEQRAC | 289 | CNRMEMPC | 290 |
| CQIRPIDKC | 291 | CAIDIGGAC | 292 |
| CGRFDTAPQRGC | 293 | CKRANRLSC | 294 |
| CLLNYTYC | 295 | CLNGLVSMC | 296 |
| CMSLGNNC | 297 | CNRNRMTPC | 298 |
| CQASASDHC | 299 | CQLINSSPC | 300 |
| CQRVNSVENASC | 301 | CRKEHYPC | 302 |
| CRRHMERC | 303 | CSGRPFKYC | 304 |
| CTHLVTLC | 305 | CTSSPAYNC | 306 |
| CVTSNLRVC | 307 | CWDSGSHIC | 308 |
| CERSHGRLC | 309 | CGNLLTRRC | 310 |
| CINCLSQC | 311 | CLRHDFYVC | 312 |
| CNSRSENC | 313 | CRYKGPSC | 314 |
| CSHHDTNC | 315 | CSRWYTTC | 316 |
| CYAGSPLC | 317 | CQTTSWNC | 318 |
| CQWSMNVC | 319 | CRARIRAEDISC | 320 |
| CRDVVSVIC | 321 | CRREYSAC | 322 |
| Pancreas: | | | |
| EICQLGSCT | 323 | WRCEGFNCQ | 324 |
| RKCLRPDCG | 325 | SWCEPGWCR | 326 |
| LACFVTGCL | 327 | GLCNGATCM | 328 |
| DMCWLIGCG | 329 | SGCRTMVCV | 330 |
| QRCPRSFCL | 331 | LSCAPVICG | 332 |
| RECTNEICY | 333 | NECLMISCR | 334 |
| SCVFCDWLS | 335 | WACEELSCF | 336 |
| QNCPVTRCV | 337 | CATLTNDEC | 338 |
| CDNREMSC | 339 | CFMDHSNC | 340 |
| CGEYGREC | 341 | CHMKRDRTC | 342 |
| CKKRLLNVC | 343 | CLDYHPKC | 344 |
| CMTGRVTC | 345 | CNKIVRRC | 346 |
| CPDLLVAC | 347 | CSDTQSIGC | 348 |
| CSKAYDLAC | 349 | CSKKGPSYC | 350 |
| CTLKHTAMC | 351 | CTQHIANC | 352 |
| CTTEIDYC | 353 | CVGRSGELC | 354 |
| Liver: | | | |
| ARRGWTL | 355 | SRRFVGG | 356 |
| QLTGGCL | 357 | ALERRSL | 358 |
| KAYFRWR | 359 | RWLAWTV | 360 |
| VGSFIYS | 361 | LSLLGIA | 362 |
| LSTVLWF | 363 | SLAMRDS | 364 |
| GRSSLAC | 365 | SELLGDA | 366 |
| CGGAGAR | 367 | WRQNMPL | 368 |
| DFLRCRV | 369 | QAGLRCH | 370 |
| RALYDAL | 371 | WVSVLGF | 372 |
| GMAVSSW | 373 | SWFFLVA | 374 |
| WQSVVRV | 375 | VKSVCRT | 376 |
| CGNGHSC | 377 | AEMEGRD | 378 |
| SLRPDNG | 379 | PAMGLIR | 380 |
| Lymph Node: | | | |
| WGCKLRFCS | 381 | MECIKYSCL | 382 |
| GICATVKCS | 383 | PRCQLWACT | 384 |
| TTCMSQLCL | 385 | SHCPMASLC | 386 |
| GCVRRLLCN | 387 | TSCRLFSCA | 388 |
| KYCTPVECL | 389 | RGCNGSRCS | 390 |
| MCPQRNCL | 391 | PECEGVSCI | 392 |
| AGCSVTVCG | 393 | IPCYWESCR | 394 |
| GSCSMFPCS | 395 | QDCVKRPCV | 396 |
| SECAYRACS | 397 | WSCARPLCG | 398 |
| SLCGSDGCR | 399 | RLCPSSPCT | 400 |

TABLE 1-continued

| | SEQ ID NO: | | SEQ ID NO: |
|---|---|---|---|
| MRCQFSGCT | 401 | RYCYPDGCL | 402 |
| STCGNWTCR | 403 | LPCTGASCP | 404 |
| CSCTGQLCR | 405 | LECRRWRCD | 406 |
| GLCQIDECR | 407 | TACKVAACH | 408 |
| DRCLDIWCL | 409 | XXXQGSPCL | 410 |
| PLCMATRCA | 411 | RDCSHRSCE | 412 |
| NPCLRAACI | 413 | PTCAYGWCA | 414 |
| LECVANLCT | 415 | RKCGEEVCT | 416 |
| EPCTWNACL | 417 | LVCPGTACV | 418 |
| LYCLDASCL | 419 | ERCPMAKCY | 420 |
| LVCQGSPCL | 421 | QQCQDPYCL | 422 |
| DXCXDIWCL | 423 | QPCRSMVCA | 424 |
| KTCVGVRV | 425 | WSCHEFNCR | 426 |
| LTCWDWSCR | 427 | SLCRLSTCS | 428 |
| KTCAGSSCI | 429 | VICTGRQCG | 430 |
| NPCFGLLV | 431 | SLCTAFNCH | 432 |
| RTCTPSRCM | 433 | QSCLWRICI | 434 |
| QYCWSKGCR | 435 | LGCFPSWCG | 436 |
| VTCSSEWCL | 437 | RLCSWGGCA | 438 |
| STCISVHCS | 439 | EVCLVLSCQ | 440 |
| IACDGYLCG | 441 | RDCVKNLCR | 442 |
| XGCYQKRCT | 443 | LGCFXSWCG | 444 |
| IRCWGGRCS | 445 | IPCSLLGCA | 446 |
| AGCVQSQCY | 447 | PRCWERVCS | 448 |
| KACFGADCX | 449 | TLCPLVACE | 450 |
| SACWLSNCA | 451 | SECYTGSCP | 452 |
| GLCQEHRCW | 453 | VECGFSAVF | 454 |
| EDCREWGCR | 455 | HWCRLLACR | 456 |
| Adrenal Gland: | | | |
| WGCKLRFCS | 457 | MECIKYSCL | 458 |
| GICATVKCS | 459 | PRCQLWACT | 460 |
| TTCMSQLCL | 461 | SHCPMASLC | 462 |
| GCVRRLLCN | 463 | TSCRLFSCA | 464 |
| KYCTPVECL | 465 | RGCNGSRCS | 466 |
| MCPQRNCL | 467 | PECEGVSCI | 468 |
| AGCSVTVCG | 469 | IPCYWESCR | 470 |
| GSCSMFPCS | 471 | QDCVKRPCV | 472 |
| SECAYRACS | 473 | WSCARPLCG | 474 |
| SLCGSDGCR | 475 | RLCPSSPCT | 476 |
| MRCQFSGCT | 477 | RYCYPDGCL | 478 |
| STCGNWTCR | 479 | LPCTGASCP | 480 |
| CSCTGQLCR | 481 | LECRRWRCD | 482 |
| GLCQIDECR | 483 | TACKVAACH | 484 |
| DRCLDIWCL | 485 | XXXQGSPCL | 486 |
| PLCMATRCA | 487 | RDCSHRSCE | 488 |
| NPCLRAACI | 489 | PTCAYGWCA | 490 |
| LECVANLCT | 491 | RKCGEEVCT | 492 |
| EPCTWNACL | 493 | LVCPGTACV | 494 |
| LYCLDASCL | 495 | ERCPMAKCY | 496 |
| LVCQGSPCL | 497 | QQCQDPYCL | 498 |
| DXCXDIWCL | 499 | QPCRSMVCA | 500 |
| KTCVGVRV | 501 | WSCHEFNCR | 502 |
| LTCWDWSCR | 503 | SLCRLSTCS | 504 |
| KTCAGSSCI | 505 | VICTGRQCG | 506 |
| NPCFGLLV | 507 | SLCTAFNCH | 508 |
| RTCTPSRCM | 509 | QSCLWRICI | 510 |
| QYCWSKGCR | 511 | LGCFPSWCG | 512 |
| VTCSSEWCL | 513 | RLCSWGGCA | 514 |
| STCISVHCS | 515 | EVCLVLSCQ | 516 |
| IACDGYLCG | 517 | RDCVKNLCR | 518 |
| XGCYQKRCT | 519 | LGCFXSWCG | 520 |
| IRCWGGRCS | 521 | IPCSLLGCA | 522 |
| AGCVQSQCY | 523 | PRCWERVCS | 524 |
| KACGGADCX | 525 | TLCPLVACE | 526 |
| SACWLSNCA | 527 | SECYTGSCP | 528 |
| GLCQEHRCW | 529 | VECGFSAVF | 530 |
| EDCREWGCR | 531 | HWCRLLACR | 532 |
| LMLPRAD | 533 | | |

In addition, peptides that may be useful for targeting tumors in vivo include, but are not limited to, the peptide sequences shown in Table 2, which have been described as potential targeting peptides for tumor cells

TABLE 2

| | | | | | |
|---|---|---|---|---|---|
| CGRECPRLCQSSC | SEQ ID NO: 534 | CGEACGGQCALPC | SEQ ID NO: 535 | PSCAYMCIT | SEQ ID NO: 536 |
| SKVLYYNWE | SEQ ID NO: 537 | CERACRNLCREGC | SEQ ID NO: 538 | CKVCNGRCCG | SEQ ID NO: 539 |
| CPTCNGRCVR | SEQ ID NO: 540 | CRNCNGRCEG | SEQ ID NO: 541 | CTECNGRCQL | SEQ ID NO: 542 |
| CAVCNGRCGF | SEQ ID NO: 543 | CWGCNGRCRM | SEQ ID NO: 544 | CVPCNGRCHE | SEQ ID NO: 545 |
| CVQCNGRCAL | SEQ ID NO: 546 | CGRCNGRCLL | SEQ ID NO: 547 | CVWCNGRCGL | SEQ ID NO: 548 |
| CEGVNGRRLR | SEQ ID NO: 549 | CGSLVRC | SEQ ID NO: 550 | SKGLRHR | SEQ ID NO: 551 |
| KMGPKVW | SEQ ID NO: 552 | NPRWFWD | SEQ ID NO: 553 | SGWCYRC | SEQ ID NO: 554 |
| CWSGVDC | SEQ ID NO: 555 | IVADYQR | SEQ ID NO: 556 | LSMFTRP | SEQ ID NO: 557 |
| CVMVRDGDC | SEQ ID NO: 558 | CGVGSSC | SEQ ID NO: 559 | CGEGHPC | SEQ ID NO: 560 |
| CPEHRSLVC | SEQ ID NO: 561 | CWRKFYC | SEQ ID NO: 562 | CPRGSRC | SEQ ID NO: 563 |
| CAQLLQVSC | SEQ ID NO: 564 | CTDYVRC | SEQ ID NO: 565 | TDCTPSRCT | SEQ ID NO: 566 |
| CTAMRNTDC | SEQ ID NO: 567 | VTCRSLMCQ | SEQ ID NO: 568 | CISLDRSC | SEQ ID NO: 569 |
| CYLVNVDC | SEQ ID NO: 570 | RHCFSQWCS | SEQ ID NO: 571 | EACEMAGCL | SEQ ID NO: 572 |
| QWCSRRWCT | SEQ ID NO: 573 | NACESAICG | SEQ ID NO: 574 | EPCEGKKCL | SEQ ID NO: 575 |
| AGCINGLCG | SEQ ID NO: 576 | KGCGTRQCW | SEQ ID NO: 577 | KRCSSSLCA | SEQ ID NO: 578 |
| LDCLSELCS | SEQ ID NO: 579 | IYCPGQECE | SEQ ID NO: 580 | EDCTSRFCS | SEQ ID NO: 581 |
| RWCREKSCW | SEQ ID NO: 582 | CNKTDGDEGVTC | SEQ ID NO: 583 | CPLCNGRCAL | SEQ ID NO: 584 |
| CEQCNGRCGQ | SEQ ID NO: 585 | CVTCNGRCRV | SEQ ID NO: 586 | CETCNGRCVG | SEQ ID NO: 587 |
| CSCCNGRCGD | SEQ ID NO: 588 | CKSCNGRCLA | SEQ ID NO: 589 | CRTCNGRCQV | SEQ ID NO: 590 |
| CASNNGRVVL | SEQ ID NO: 591 | CSKCNGRCGH | SEQ ID NO: 592 | CGECNGRCVE | SEQ ID NO: 593 |
| CEVCNGRCAL | SEQ ID NO: 594 | HHTRFVS | SEQ ID NO: 595 | WRVLAAF | SEQ ID NO: 596 |
| SPGSWTW | SEQ ID NO: 597 | IKARASP | SEQ ID NO: 598 | LWAEMTG | SEQ ID NO: 599 |
| SKSSGVS | SEQ ID NO: 600 | VVDRFPD | SEQ ID NO: 601 | IMYPGWL | SEQ ID NO: 602 |
| CQLAAVC | SEQ ID NO: 603 | CGLSDSC | SEQ ID NO: 604 | CELSLISKC | SEQ ID NO: 605 |
| CYVELHC | SEQ ID NO: 606 | CYSYFLAC | SEQ ID NO: 607 | CDDSWKC | SEQ ID NO: 608 |
| CKALSQAC | SEQ ID NO: 609 | VPCRFKQCW | SEQ ID NO: 610 | CMEMGVKC | SEQ ID NO: 611 |
| CGTRVDHC | SEQ ID NO: 612 | CYLGVSNC | SEQ ID NO: 613 | LVCLPPSCE | SEQ ID NO: 614 |
| ISCAVDACL | SEQ ID NO: 615 | RSCIKHQCP | SEQ ID NO: 616 | GICKDLWCQ | SEQ ID NO: 617 |
| NRCRGVSCT | SEQ ID NO: 618 | FGCVMASCR | SEQ ID NO: 619 | DTCRALRCN | SEQ ID NO: 620 |
| YRCIARECE | SEQ ID NO: 621 | QACPMLLCM | SEQ ID NO: 622 | HTCLVALCA | SEQ ID NO: 623 |
| RKCEVPGCQ | SEQ ID NO: 624 | EICVDGLCV | SEQ ID NO: 625 | RPCGDQACE | SEQ ID NO: 626 |
| CEMCNGRCMG | SEQ ID NO: 627 | CGVCNGRCGL | SEQ ID NO: 628 | CVLCNGRCWS | SEQ ID NO: 629 |
| CRTCNGRCLE | SEQ ID NO: 630 | CRDLNGRKVM | SEQ ID NO: 631 | CPLCNGRCAR | SEQ ID NO: 632 |
| CQSCNGRCVR | SEQ ID NO: 633 | CRCCNGRCSP | SEQ ID NO: 634 | CWLCNGRCGR | SEQ ID NO: 635 |
| CIRCNGRCSV | SEQ ID NO: 636 | CLSCNGRCPS | SEQ ID NO: 637 | GRSQMQI | SEQ ID NO: 638 |
| VASVSVA | SEQ ID NO: 639 | IFSGSRE | SEQ ID NO: 640 | GRWYKWA | SEQ ID NO: 641 |
| ALVGLMR | SEQ ID NO: 642 | DTLRLRI | SEQ ID NO: 643 | VWRTGHL | SEQ ID NO: 644 |
| GLPVKWS | SEQ ID NO: 645 | CVRIRPC | SEQ ID NO: 646 | CVSGPRC | SEQ ID NO: 647 |
| CYTADPC | SEQ ID NO: 648 | CLVVHEAAC | SEQ ID NO: 649 | CFWPNRC | SEQ ID NO: 650 |
| CRLGIAC | SEQ ID NO: 651 | CYPADPC | SEQ ID NO: 652 | CGETMRC | SEQ ID NO: 653 |

TABLE 2-continued

| | | | | | |
|---|---|---|---|---|---|
| SWCQFEKCL | SEQ ID NO: 654 | CRESLKNC | SEQ ID NO: 655 | CNNVGSYC | SEQ ID NO: 656 |
| CAMVSMED | SEQ ID NO: 657 | CIRSAVSC | SEQ ID NO: 658 | FYCPGVGCR | SEQ ID NO: 659 |
| PRCESQLCP | SEQ ID NO: 660 | MFCRMRSCD | SEQ ID NO: 661 | APCGLLACI | SEQ ID NO: 662 |
| ADCRQKPCL | SEQ ID NO: 663 | RSCAEPWCY | SEQ ID NO: 664 | GRCVDGGCT | SEQ ID NO: 665 |
| ICLLAHCA | SEQ ID NO: 666 | AGCRVESC | SEQ ID NO: 667 | RLCSLYGCV | SEQ ID NO: 668 |
| LECVVDSCR | SEQ ID NO: 669 | FRCLERVCT | SEQ ID NO: 670 | CNGRCVSGCAGRC | SEQ ID NO: 671 |
| IWSGYGVYW | SEQ ID NO: 672 | WESLYFPRE | SEQ ID NO: 673 | CGLMCQGACFDVC | SEQ ID NO: 674 |
| CPRGCLAVCVSQC | SEQ ID NO: 675 | RLCRIVVIRVCR | SEQ ID NO: 676 | | |

| | |
|---|---|
| YVPLPNVPQPGRRPFPTFPGQGPFNPKIKWPQGY | SEQ ID NO: 677 |
| VFIDILDKVENAIHNAAQVGIGFAKPFEKHLINPK | SEQ ID NO: 678 |
| GNNRPVYIPQPRPPHPRI | SEQ ID NO: 679 |
| GNNRPVYIPQPRPPHPRL | SEQ ID NO: 680 |
| GNNRPIYIPQPRPPHPRL | SEQ ID NO: 681 |
| RFRPPIRRPPIRPPFYPPFRPPIRPPIFPPIRPPFRPPLRFP | SEQ ID NO: 682 |
| RRIRPRPPRLPRPRPRPLPFRPGPRPIPRPLPFRPGPRPIPRLP LPFFRPGPRPIPRP | SEQ ID NO: 683 |
| PRPIPRPLPFFRPGPRPIPR | SEQ ID NO: 684 |
| WNPFKELERAGQRVRDAVISAAPAVATVGQAALARG | SEQ ID NO: 685 |
| WNPFKELERAGQRVRDAIISAGPAVATVGQAAAIA | SEQ ID NO: 686 |
| WNPFKELERAGQRVRDAIISAAPAVATVGQAAAIARG | SEQ ID NO: 687 |
| WNPFKELERAGQRVRDAVISAAPAVATVGQAAAIARGG | SEQ ID NO: 688 |
| GIGALSAKGALKGLAKGLAZHFAN | SEQ ID NO: 689 |
| GIGASILSAGKSALKGLAKGLAEHFAN | SEQ ID NO: 690 |
| GIGSAILSAGKSALKGLAKGLAEHFAN | SEQ ID NO: 691 |
| IKITTMLAKLGKVLAHV | SEQ ID NO: 692 |
| SKITDILAKLGKVLAIIV | SEQ ID NO: 693 |
| RPDFCLEPPYTGPCKARII | SEQ ID NO: 694 |
| RYFYNAKAGLCQTFVYG | SEQ ID NO: 695 |
| GCRAKRINNFKSAEDCMRTCGGA | SEQ ID NO: 696 |
| FLPLLAGLAANFLPKIFCKITRKC | SEQ ID NO: 697 |
| GIMDTLKNLAKTAGKGALQSLLNKASCKLSGQC | SEQ ID NO: 698 |
| KWKLFKKIEKVGQNIRDGIIKAGPAVAVVGQATQIAK | SEQ ID NO: 699 |
| KWKVFKIKIEKMGRNIRNGIVKAGPAIAVLGEAKAL | SEQ ID NO: 700 |
| GWILKKLGKRIERIGQHTRDATIQGLGIAQQAANVAATARG | SEQ ID NO: 701 |
| WNPFKELEKVGQRVRDAVISAGPAVATVAQATALAK | SEQ ID NO: 702 |
| SWLSKTAKKLENSAKKRISEGIAIAIQGGPR | SEQ ID NO: 703 |
| ZFTNVSCTTSKECWSVCQRLHNTSRGKCMNKKCRCYS | SEQ ID NO: 704 |
| FLPLILRKIVTAL | SEQ ID NO: 705 |
| LRDLVCYCRSRGCKGRERMNGTCRKGHLLYTLCCR | SEQ ID NO: 706 |
| LRDLVCYCRTRGCKRRERMNGTCRKGHLMYTLCCR | SEQ ID NO: 707 |

TABLE 2-continued

| Sequence | SEQ ID NO |
|---|---|
| VVCACRRALCLPRERRAGFCRIRGRIHTPLCCRR | SEQ ID NO: 708 |
| VVCACRRALCLPLERRAGFCRIRGRIHPLCCRR | SEQ ID NO: 709 |
| RRCICTTRTCRFPYRRLGTCIFQNRVYTFCC | SEQ ID NO: 710 |
| RRCICTTRTCRFPYRRLGTCLFQNRVYTFCC | SEQ ID NO: 711 |
| ACYCRIPACIAGERRYGTCIYQGRLWAFCC | SEQ ID NO: 712 |
| CYCRIPACIAGERRYGTCIYQGRLWAFCC | SEQ ID NO: 713 |
| VVCACRRALCLPRERRAGFCRIRGRIHPLCCRR | SEQ ID NO: 714 |
| VVCACRRALCLPLERRAGFCRIRGRIHPLCCRR | SEQ ID NO: 715 |
| VTCYCRRTRCGFRERLSGACGYRGRIYRLCCR | SEQ ID NO: 716 |
| VTCYCRSTRCGFRERLSGACGYRGRIYRLCCR | SEQ ID NO: 717 |
| DFASCHTNGGICLPNRCPGHMIQIGICFRPRVKCCRSW | SEQ ID NO: 718 |
| VRNHVTCRINRGFCVPIRCPGRTRQIGTCFGPRIKCCRSW | SEQ ID NO: 719 |
| NPVSCVRNKGICVPIRCPGSMKQIGTCVGRAVKCCRKK | SEQ ID NO: 720 |
| ATCDLLSGTGINHSACAAHCLLRGNRGGYCNGKAVCVCRN | SEQ ID NO: 721 |
| GFGCPLDQMQCHRHCQTITGRSGGYCSGPLKLTCTCYR | SEQ ID NO: 722 |
| GFGCPLNQGACHRHCRSIRRRGGYCAGFFKQTCTCYRN | SEQ ID NO: 723 |
| ALWKTMLKKLGTMALHAGKAALGAADTISQTQ | SEQ ID NO: 724 |
| GKPRPYSPRPTSHPRPIRV | SEQ ID NO: 725 |
| GIFSKLGRKKIKNLLISGLKNVGKEVGMDVVRTGIDIAGCKIKGEC | SEQ ID NO: 726 |
| ILPWKWPWWPWRR | SEQ ID NO: 727 |
| FKCRRWQWRMKKLGAPSITCVRRAP | SEQ ID NO: 728 |
| ITSISLCTPGCKTGALMGCNMKTATCHCSIHVSK | SEQ ID NO: 729 |
| TAGPAIRASVKQCQKTLKATRLFTVSCKGKNGCK | SEQ ID NO: 730 |
| MSKFDDFDLDVVKVSKQDSKITPQWKSESLCTPGCVTGALQTCFLQTLTCNCKISK | SEQ ID NO: 731 |
| KYYGNGVHCTKSGCSVN | SEQ ID NO: 732 |
| WGEAFSAGVHRLANGGNGFW | SEQ ID NO: 733 |
| GIGKFLHSAGKFGKAFVGEIMKS | SEQ ID NO: 734 |
| GIGKFLHSAKKFGKAFVGEIMNS | SEQ ID NO: 735 |
| GMASKAGAIAGKIAKVALKAL | SEQ ID NO: 736 |
| GVLSNVIGYLKKLGTGALNAVLKG | SEQ ID NO: 737 |
| GWASKIGQTLGKIAKVGLKELIQPK | SEQ ID NO: 738 |
| INLKALAALAKKIL | SEQ ID NO: 739 |
| GIGAVLKVLTTGLPALISWIKRKRQQ | SEQ ID NO: 740 |
| ATCDLLSGTGINHSACAAHCLLRGNRGGYCNGKGVCVCRN | SEQ ID NO: 741 |
| ATCDLLSGTGINHSACAAHCLLRGNRGGYCNRKGVCVRN | SEQ ID NO: 742 |
| RRWCFRVCYRGFCYRKCR | SEQ ID NO: 743 |
| RRWCFRVCYKGFCYRKCR | SEQ ID NO: 744 |
| RGGRLCYCRRRFCVCVGR | SEQ ID NO: 745 |
| RGGRLCYCRRRFCICV | SEQ ID NO: 746 |

TABLE 2-continued

| | |
|---|---|
| RGGGLCYCRRRFCVCVGR | SEQ ID NO: 747 |
| VTCDLLSFKGQVNDSACAANCLSLGKAGGHCEKGVCICRKTSFKDL WDKYF | SEQ ID NO: 748 |
| GWLKKIGKKIERVGQHTRDATIQGLGIAQQAANVAATAR | SEQ ID NO: 749 |
| GWLKKIGKKIERVGQHTRDATIQVIGVAQQAANVAATAR | SEQ ID NO: 750 |
| SDEKASPDKHHRFSLSRYAKLANRLANPKLLETFLSKWIGDRGNRSV | SEQ ID NO: 751 |
| KWCFRVCYRGICYRRCR | SEQ ID NO: 752 |
| RWCFRVCYRGICYRKCR | SEQ ID NO: 753 |
| KSCCKDTLARNCYNTCRFAGGSRPVCAGACRCKIIGPKCPSDYPK | SEQ ID NO: 754 |
| GGKPDLRPCIIPPCHYIPRPKPR | SEQ ID NO: 755 |
| VKDGYIVDDVNCTYFCGRNAYCNEECTKLKGESGYCQWASPYGNAC YCKLPDHVRTKGPGRCH | SEQ ID NO: 756 |

Incorporation of a targeting peptide or other targeting moiety into the outer shell may be accomplished by any of the methods known in the art of targeted drug delivery. Suitable methods include but are not limited to covalent attachment of a targeting moiety to one or more components of the outermost shell, either directly or via linkers and electrostatic binding of appropriately charged molecules. These and other methods are well known in the art; see for example A. Coombes et al., *Biomaterials* 18:1153-1161, 1997.

Another aspect of the invention relates to the functionalization of the surface of the micelles with one or more imaging agents. An "imaging agent" is a moiety suitable for generating a detectable signal, e.g., using a technique such as positron emission tomography (PET), single photon emission tomography (SPECT), or magnetic resonance imaging (MRI), such as a radionuclides, unpaired spin atoms and free radicals (e.g., Fe, lanthanides, and Gd), and contrast agents (e.g., chelated (DTPA) manganese). A number of suitable imaging agents that can be employed in the micelles of the present invention are disclosed in U.S. Patent Application No. 2003-0049203, which is hereby incorporated herein by reference in its entirety.

For example, SPECT can be used for molecular imaging studies to assess both drug distribution and physiological effects with high sensitivity of detection. Furthermore, the use of SPECT allows the simultaneous observation of multiple probes with different emission wavelengths. In certain embodiments, the radioactive moiety is selected from $^{225}$Ac, $^{227}$Ac, $^{241}$Am, $^{72}$As, $^{74}$As, $^{211}$At, $^{198}$Au, $^{7}$Be, $^{212}$Bi, $^{213}$Bi, $^{75}$Br, $^{77}$Br, $^{11}$C, $^{14}$C, $^{48}$Ca, $^{109}$Cd, $^{139}$Ce, $^{141}$Ce, $^{252}$Cf, $^{55}$Co, $^{57}$Co, $^{60}$Co, $^{51}$Cr, $^{130}$Cs, $^{131}$Cs, $^{137}$Cs, $^{61}$Cu, $^{62}$Cu, $^{165}$Dy, $^{152}$Eu, $^{155}$Eu, $^{18}$F, $^{55}$Fe, $^{59}$Fe, $^{64}$Ga, $^{67}$Ga, $^{68}$Ga, $^{153}$Gd, $^{68}$Ge, $^{3}$H, $^{122}$I, $^{123}$I, $^{124}$I, $^{125}$I, $^{131}$I, $^{132}$I, $^{111}$In, $^{115m}$In, $^{191m}$Ir, $^{192}$Ir, $^{81m}$Kr, $^{177}$Lu, $^{51}$Mn, $^{52}$Mn, $^{99}$Mo, $^{13}$N, $^{95}$Nb, $^{15}$O, $^{191}$Os, $^{194}$Os, $^{32}$P, $^{33}$P, $^{203}$Pb, $^{212}$Pb, $^{103}$Pd, $^{109}$Pd, $^{238}$Pu, $^{223}$Ra, $^{226}$Ra, $^{82}$Rb, $^{186}$Re, $^{188}$Re, $^{105}$Rh, $^{97}$Ru, $^{103}$Ru, $^{35}$S, $^{72}$Se, $^{75}$Se, $^{28}$Si, $^{145}$Sm, $^{153}$Sm, $^{117m}$Sn, $^{85}$Sr, $^{89}$Sr, $^{90}$Sr, $^{178}$Ta, $^{179}$Ta, $^{182}$Ta, $^{149}$Tb, $^{96}$Tc, $^{99m}$Tc, $^{228}$Th, $^{229}$Th, $^{201}$Tl, $^{170}$Tm, $^{171}$Tm, $^{188}$W, $^{127}$Xe, $^{88}$Y, $^{90}$Y, $^{91}$Y, $^{169}$Yb, $^{62}$Zn, $^{65}$Zn, $^{95}$Zr, and $^{99m}$Tc-labeled Annexin V$^{28}$. Additionally, $^{99m}$Tc-labeled Annexin V$^{28}$ is an available apoptosis probe available when using SPECT, wherein Annexin V is a human protein known to bind phosphatidylserine on the exterior of apoptotic cells.

In certain embodiments, the imaging moiety may be incorporated onto the surface of the micellar structure by fabricating a micelle with a chelating group on the surface that is capable of chelating an imaging moiety. This can be accomplished by, for example, synthesizing block copolymers of PEG and PCL, some of which contain a terminal methyl group (MPEG-PCL), and others in which the PEG chain is covalently linked to the chelating group.

In certain embodiments, the chelating group is selected from 1,4,7,10-tetraazacyclododecane-1,4,7,10-tetraacetic acid (DOTA), diethylenetriaminepentaacetic acid bis(methylamide) (DTPA-BMA), N,N'-bis(2-pyridylmethyl)diethylenetriamine-N,N',N''-triacetic acid (DTPA-BP), and trans-1,2-diaminocyclohexane-N,N',N'',N'''-tetraacetic acid (CDTA). In preferred embodiments, the chelating group is DOTA.

Examples of radioactive imaging moieties include, but are not limited to, $^{225}$Ac, $^{227}$Ac, $^{241}$Am, $^{72}$As, $^{74}$As, $^{211}$At, $^{198}$Au, $^{7}$Be, $^{212}$Bi, $^{213}$Bi, $^{75}$Br, $^{77}$Br, $^{11}$C, $^{14}$C, $^{48}$Ca, $^{109}$Cd, $^{139}$Ce, $^{141}$Ce, $^{252}$Cf, $^{55}$Co, $^{57}$Co, $^{60}$Co, $^{51}$Cr, $^{130}$Cs, $^{131}$Cs, $^{137}$Cs, $^{61}$Cu, $^{62}$Cu, $^{165}$Dy, $^{152}$Eu, $^{155}$Eu, $^{18}$F, $^{55}$Fe, $^{59}$Fe, $^{64}$Ga, $^{67}$Ga, $^{68}$Ga, $^{153}$Gd, $^{68}$Ge, $^{3}$H, $^{122}$I, $^{123}$I, $^{124}$I, $^{125}$I, $^{131}$I, $^{132}$I, $^{111}$In, $^{115m}$In, $^{191m}$Ir, $^{192}$Ir, $^{81m}$Kr, $^{177}$Lu, $^{51}$Mn, $^{52}$Mn, $^{99}$Mo, $^{13}$N, $^{95}$Nb, $^{15}$O, $^{191}$Os, $^{194}$Os, $^{32}$P, $^{33}$P, $^{203}$Pb, $^{212}$Pb, $^{103}$Pd, $^{109}$Pd, $^{238}$Pu, $^{223}$Ra, $^{226}$Ra, $^{82}$Rb, $^{186}$Re, $^{188}$Re, $^{105}$Rh, $^{97}$Ru, $^{103}$Ru, $^{35}$S, $^{72}$Se, $^{75}$Se, $^{28}$Si, $^{145}$Sm, $^{153}$Sm, $^{117m}$Sn, $^{85}$Sr, $^{89}$Sr, $^{90}$Sr, $^{178}$Ta, $^{179}$Ta, $^{182}$Ta, $^{149}$Tb, $^{96}$Tc, $^{99m}$Tc, $^{228}$Th, $^{229}$Th, $^{201}$Tl, $^{170}$Tm, $^{171}$Tm, $^{188}$W, $^{127}$Xe, $^{88}$Y, $^{90}$Y, $^{91}$Y, $^{169}$Yb, $^{62}$Zn, $^{65}$Zn, $^{95}$Zr, and $^{99m}$Tc-labeled Annexin V$^{28}$. In preferred embodiments, the radioactive moiety is capable of being chelated by a chelating agent and is selected from $^{225}$Ac, $^{227}$Ac, $^{241}$Am, $^{198}$Au, $^{7}$Be, $^{212}$Bi, $^{213}$Bi, $^{48}$Ca, $^{109}$Cd, $^{139}$Ce, $^{141}$Ce, $^{252}$Cf, $^{55}$Co, $^{57}$Co, $^{60}$Co, $^{51}$Cr, $^{130}$Cs, $^{131}$Cs, $^{137}$Cs, $^{61}$Cu, $^{62}$Cu, $^{165}$Dy, $^{152}$Eu, $^{155}$Eu, $^{18}$F, $^{55}$Fe, $^{59}$Fe, $^{64}$Ga, $^{67}$Ga, $^{68}$Ga, $^{153}$Gd, $^{68}$Ge, $^{111}$In, $^{115m}$In, $^{191m}$Ir, $^{192}$Ir, $^{177}$Lu, $^{51}$Mn, $^{52}$Mn, $^{99}$Mo, $^{95}$Nb, $^{194}$Os, $^{203}$Pb, $^{212}$Pb, $^{103}$Pd, $^{109}$Pd, $^{238}$Pu, $^{223}$Ra, $^{226}$Ra, $^{82}$Rb, $^{186}$Re, $^{188}$Re, $^{105}$Rh, $^{97}$Ru, $^{103}$Ru, $^{145}$Sm, $^{153}$Sm, $^{117m}$Sn, $^{85}$Sr, $^{89}$Sr, $^{90}$Sr, $^{178}$Ta, $^{179}$Ta, $^{182}$Ta, $^{149}$Tb, $^{96}$Tc, $^{99m}$Tc, $^{228}$Th, $^{229}$Th, $^{201}$Tl, $^{170}$Tm, $^{171}$Tm, $^{188}$W, $^{88}$Y, $^{90}$Y, $^{91}$Y, $^{169}$Yb, $^{62}$Zn, $^{65}$Zn, $^{99m}$Tc-labeled Annexin V$^{28}$, and $^{95}$Zr. In certain embodiments, the radioactive moiety is $^{111}$In, $^{99m}$Tc-labeled Annexin V$^{28}$, or $^{99m}$Tc. In certain such embodiments, the radioactive moiety is $^{111}$In.

Yet another aspect of the invention relates to micelles containing within the hydrophobic core, a magnetic resonance imaging (MRI) contrast imaging agent either alone or in combination with another hydrophobic agent and/or functionalization of the corona of the micelle. Examples of such contrast agents, include, but are not limited to, gadopentetate dimeglumine, gadoteridol, gadoterate meglumine, mangafodipir trisodium, gadodiamide, gadoversetamide, and superparamagnetic iron oxide. Superparamagnetic iron oxide (SPIO) nanoparticles are a class of MRI contrast agents that provide extremely strong enhancement of proton relaxation. In contrast to low molecular weight "T1" paramagnetic metal chelates such as Gd-DTPA, SPIO nanoparticles are classified as T2 negative contrast agents, with MR sensitivity approximately 1000 times higher than T1 agents. SPIO agents are composed of iron oxide nanocrystals which create a large, dipolar magnetic field gradient that creates a relaxation effect on nearby water molecules. According to their sizes and applications, SPIO nanoparticles have been classified into four different categories: large, standard, ultrasmall, and monocrystalline agents. Large SPIO agents are mainly used for gastrointestinal lumen imaging, while standard SPIO agents are used for liver and spleen imaging. When the SPIO nanoparticles are in the range of 20-40 nm (ultrasmall category), they can be injected to visualize lymph node metastases. The smallest monocrystalline SPIO agents are used for tumor-specific imaging when attached to monoclonal antibodies, growth factors, and antigens.

In preferred embodiments, the MRI contrast imaging agent is superparamagnetic iron oxide (SPIO). FIG. 8A shows a transmission electron micrograph of a typical micelle containing numerous individual SPIO particles, wherein the white circle denotes the approximate boundary of the micelle core.

Another aspect of the invention relates to method for the treatment of cancer, comprising administering micelles of the present invention, wherein the micellar structure comprises an encapsulated chemotherapeutic agent. In certain such embodiments, the coronas of the micelles are functionalized with peptides that are capable of targeting tumor cells. Additionally, or alternatively, the corona of the micelle is functionalized with a peptide that is capable of targeting a specific tissue in the body, preferably a peptide selected from either Table 1 or 2.

In certain embodiments, the coronas of the micelles are functionalized with chelating agents that are capable of chelating a radioactive moiety. In preferred such embodiments, the micelles further comprise a radioactive moiety that is capable of being chelated by the chelating agent. A further aspect of the invention relates to a method for monitoring the delivery of a hydrophobic agent, comprising administering micelles, wherein the micellar structure comprises an encapsulated hydrophobic agent, and the hydrophobic agent is an MRI contrast agent. In preferred embodiments, the micellar structure further comprises a functionalized corona and/or an additional hydrophobic agent. In more preferred embodiments, the additional hydrophobic agent is a chemotherapeutic agent.

Another aspect of the invention is a pharmaceutical composition, comprising micelles as described herein and a pharmaceutically acceptable carrier.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

As used herein, the term "treating" or "treatment" includes reversing, reducing, or arresting the symptoms, clinical signs, and underlying pathology of a condition in manner to improve or stabilize a subject's condition.

The present invention may be further appreciated upon consideration of the following illustrative and non-limiting examples.

EXAMPLES

Synthesis of Diblock Copolymers of PCL and MPEG

Detailed synthetic method for this class of block copolymers was described in a recent publication (X. Shuai et al., Macromolecules (2003) 36 5751-5759. Briefly, the diblock copolymers (MPEG-b-PCL), with yields >95%, were synthesized by ring-opening polymerization of s-caprolactone at 115° C. using MPEG as a macro-initiator and $Sn(Oct)_2$ as a catalyst. The degree of polymerization of the PCL block was calculated by comparing integrals of characteristic peaks of the PCL block at ~2.25 ppm and PEG block at 3.35 ppm in the $^1H$ NMR spectrum.

Characterization of Copolymers

Fourier transform infrared (FTIR) spectral studies were carried out with a BIO-RAD FTS-575C FTIR spectrometer in the range between 4000 and 750 $cm^{-1}$, with a resolution of 2 $cm^{-1}$. Powdery samples were compressed into KBr pellets for the FTIR measurements. $^1H$ NMR spectra were recorded on a Varian 600-MHz NMR spectrometer in deuterated water ($D_2O$) or chloroform ($CDCl_3$) at room temperature.

Gel permeation chromatography (GPC) was employed to determine the molecular weight and the molecular weight distribution. GPC analysis was carried out using a PLgel 5 μm Mixed-D 300×7.5 mm column (Polymer Laboratories) with THF as an eluent (1 mL/min) and polystyrene standards for column calibration. 20 μL samples were injected. The eluent was analyzed with a Perkin-Elmer Series 200 differential refractive index (RI) detector.

Preparation of DOX-Loaded Micelles

Polymeric micelles containing DOX were prepared as following: MPEG-b-PCL copolymer (10 mg) and doxorubicin (2 mg) were dissolved in THF (2 mL) in a glass vial. Afterwards, the solution was added dropwise to pure water (20 mL) under vigorous ultrasonic agitation using a Type 60 Sonic Dismembrator (Fisher Scientific) at a power level of 10. The beaker was then open to air overnight, allowing slow evaporation of THF and formation of micelles. The residual THF was completely removed by vacuum distillation with a rotary evaporator. The micelle solution concentrated to 5 mL was filtered with a syringe filter (pore size: 0.45 μm) to eliminate the polymer and DOX aggregates, and then filtered through a MILLIPORE Centrifugal Filter Device (Mw cut-off: 100,000 Da) to remove free DOX dissolved in the micelle solution.

The micelles thus obtained were characterized with photon correlation spectroscopy. Measurements were performed at 25° C. on a 90 Plus Particle Size Analyzer from Brookhaven Instruments Corporation. Scattered light was detected at 90° angle and collected on an autocorrelator. For each sample, data obtained from five measurements were averaged to yield the size and size distribution.

Determination of DOX-Loading Content (DLC)

The DOX-loading content (DLC) was defined as the weight percentage of DOX in the micelle. DLC was quantified by determining the absorbance at 485 nm using a Perkin-Elmer Lambda 20 UV-Vis spectrophotometer. First, the micelle solutions were frozen and lyophilized to yield the solid micelle samples. Then the dried samples were redissolved in a mixture of chloroform and DMSO (1:1, v/v) for the UV-Vis measurement. DOX solutions of various concentrations were prepared, and the absorbance at 485 nm was measured to generate a calibration curve for the DLC calculations from various micelles.

In Vitro Release of DOX from Polymer Micelles

Freeze-dried micelle samples (15 mg each) were re-suspended in PBS or acetate buffered solutions and transferred into dialysis tubing (Mw cut-off: 50,000 Da, supplied by Spectrum Laboratories Inc., USA). The tubing was placed into 50 mL PBS or acetate buffered solutions. Release study was performed at 37° C. in a New Brunswick Scientific C24 Incubator Shaker. At selected time intervals, buffered solution outside the dialysis bag was removed for UV-Vis analysis and replaced with fresh buffer solution. DOX concentration was calculated based on the absorbance intensity at 485 nm.

Hemolysis Study

Blood was freshly obtained from a male beagle dog and collected in heparin-coated tubes. Blood was washed three times with PBS and collected by centrifugation at 2,800 rpm for 5 min. Micelle solutions were prepared at different concentrations in the PBS buffer, and 100 μL of the erythrocyte suspension were added to 900 μl of micelle solutions. The samples were incubated for 60 min at 37° C. in a New Brunswick Scientific C24 Incubator Shaker. The release of hemoglobin was measured by UV-Vis analysis of the supernatant at 540 nm after centrifugation at 12,000 g for 60 min. The complete hemolysis was achieved by incubating the same amount of erythrocytes with 0.2% Triton X-100, and all hemolysis data points are presented as the percentage of the complete hemolysis.

Confocal Laser Scanning Microscopy (CLSM)

Free DOX and DOX-containing micelles were incubated in MCF-7 cell culture for 2 and 24 hours before confocal laser scanning microscopy (CLSM) examination. To identify the micelle location, cell nuclei were stained with Hoechst 33342 (Molecular Probes, Inc.) and culture media were replaced with PBS during microscopy. Samples were examined by CLSM using a Zeiss LSM 510 (Zurich, Switzerland) with a confocal plane of 300 nm. Hoechst 33342 and DOX were excited at 352 and 485 nm with emissions at 455 and 595 nm, respectively.

In Vitro Cytotoxicity Study Against MCF-7 Breast Tumor Cells

Human MCF-7 breast cancer cells were seeded onto 48-well plates with a seeding density of 7,000 cells/well. Cells were maintained in Roswell Park Memorial Institute (RPMI-1640, Sigma) media supplemented with 5% heat-inactivated fetal bovine serum, 2 mM L-glutamine, 5,000 units/ml penicillin, 5 mg/ml streptomycin, 0.1 mg/ml gentamicin sulfate and Amphotericin-B, 25 mM KCl, 25 mM D-glucose, and incubated at 37° C. in a humidified atmosphere with 5% $CO_2$. Cells were incubated for one day, and then micelle or free DOX solutions were added. After one or five days, cells were harvested and DNA levels were analyzed through a DNA assay with a Perkin-Elmer HTS 7000 Bioassay Reader. The cytotoxicity of DOX and DOX-containing micelles in aqueous solution was analyzed and compared.

Synthesis of Maleimide-Terminated Block Copolymer (MAL-PEG-PCL)

In contrast to the reported ε-caprolactone polymerization procedure with stannous (II) octoate as a catalyst (X. Shuai, T. Merdan, A. K. Schaper, F. Xi, T. Kissel, *Bioconjug. Chem.* (2004) 15 441-448), synthesis of MAL-PEG-PCL, as shown in FIG. 1, must be conducted at a lower temperature due to the thermal susceptibility of the maleimide end groups. Reaction at 68° C. led to desired molecular weights of PCL segments (e.g., 2.4 kD), while greatly reducing the thermal decomposition of maleimide to a negligible level. DOX-loaded, MAL-PEG-PCL micelles were prepared by a solvent-evaporation method. Different amounts of methoxy-terminated MPEG-PCL copolymer were also introduced to control maleimide density at the micelle surface, which subsequently controls the cRGD density (5, 16, and 76% of all PEG chains).

Figure 2:
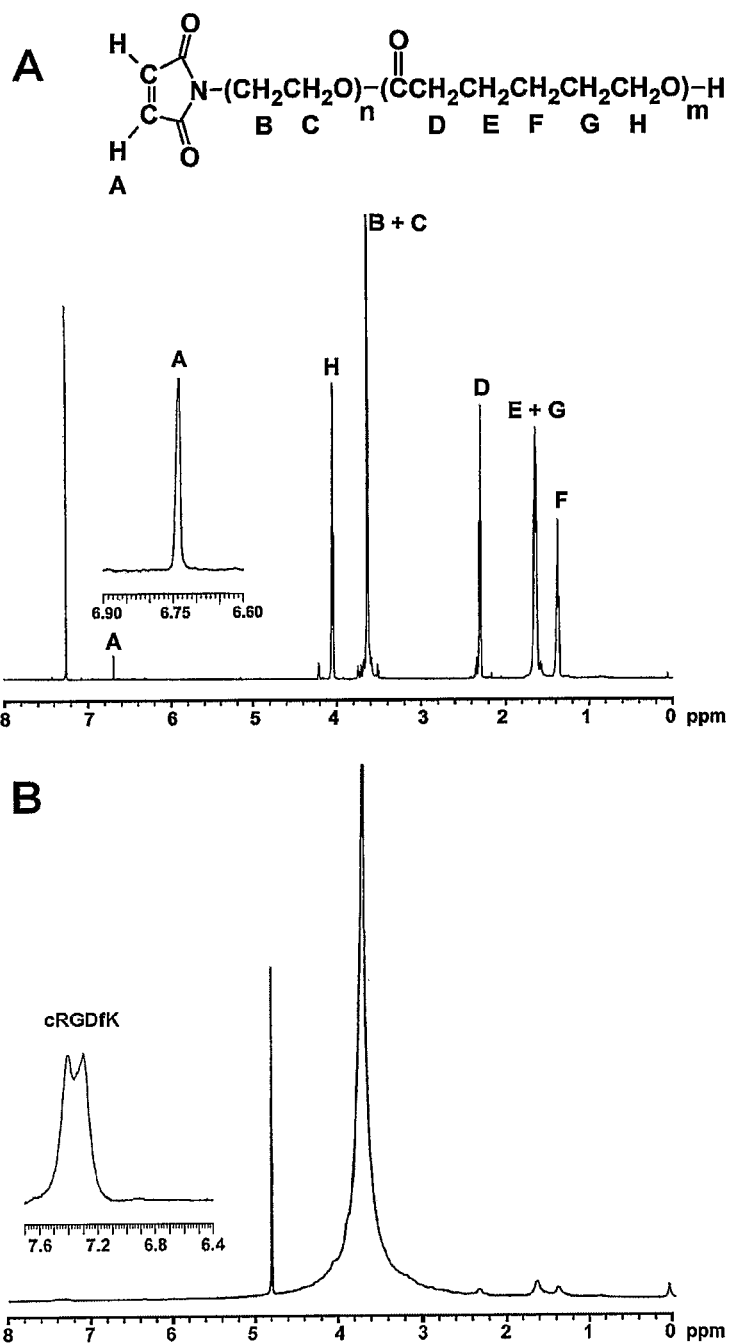
FIG. 2a shows the $^1$H NMR of MAL-PEG-PCL in CDCl$_3$.
FIG. 2b shows an expanded $^1$H NMR of MAL-PEG-PCL in CDCl$_3$.

FIG. 2a shows the $^1$H NMR spectrum of MAL-PEG-PCL copolymer in $CDCl_3$. Resonances of the PEG methylene protons (mainly at 3.64 ppm) and PCL protons (1.38, 1.65, 2.31 and 4.06 ppm) were observed. A small triplet shown at 4.2 ppm was attributed to proton resonance of the methyleneoxyl group linking PCL and PEG blocks. The integration intensity of maleimide vinyl protons at 6.74 ppm confirms that the maleimide group in MAL-PEG-PCL copolymers remained intact as in the MAL-PEG-OH. These data strongly demonstrated that the desired block copolymers were successfully synthesized. The number-averaged molecular weight of PCL blocks was calculated to be 2.4 kD using the integral intensity of PCL proton at 2.31 ppm versus that of the PEG proton at 3.64 ppm. To ensure the localization of cRGD on the surface of micelles, we used a post-micellar modification strategy to prepare cRGD-functionalized micelles as shown in FIG. 1. The NMR spectrum of the freeze-dried micelles in $D_2O$ strongly suggests the core-shell structure of DOX-loaded micelles as shown in FIG. 2b. The micelle corona shells consisting of PEG blocks were well solvated in $D_2O$ and showed clear $^1$H NMR signals. In contrast, DOX was loaded inside the solid PCL cores of micelles, and thus resonance peaks of both PCL blocks and DOX molecules were significantly reduced due to their insufficient chain mobility in $D_2O$. Moreover, successful conjugation of cRGDfK onto the well-solvated PEG corona shells was verified by the resonance peaks of phenyl protons of cRGDfK at 7.4 ppm and complete disappearance of maleimide peak at 6.74 ppm (FIG. 1B).

Synthesis of cRGD Using Solid Phase Peptide Synthesis Chemistry

Figure 3:
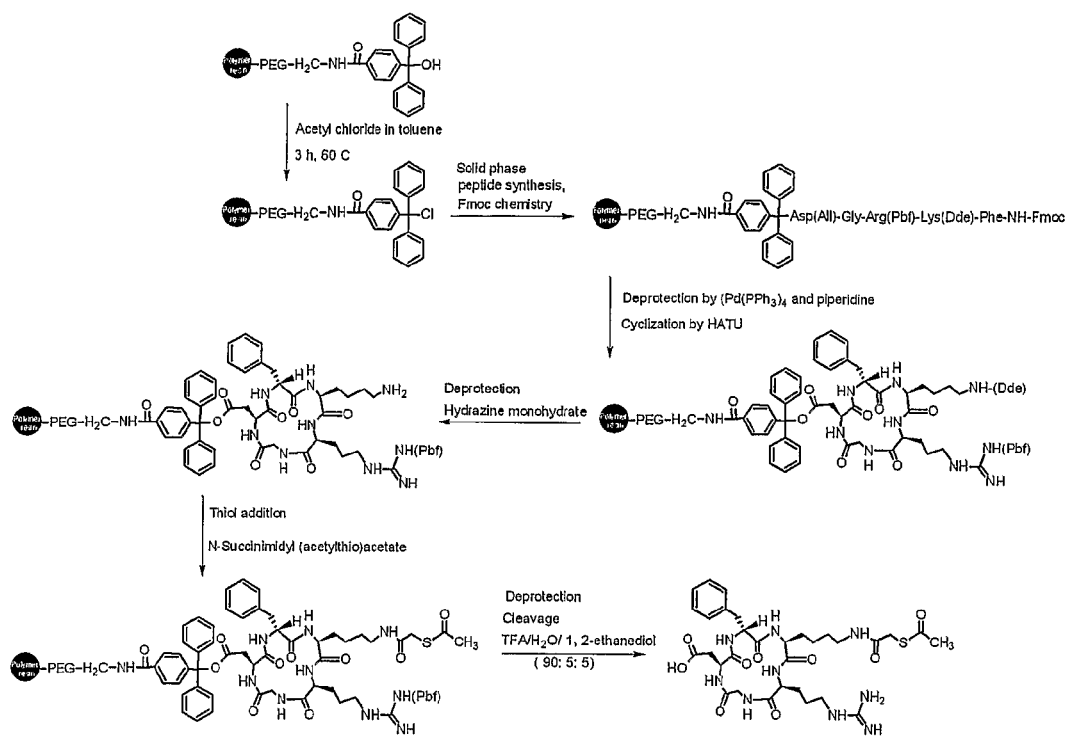
FIG. 3 shows the synthesis of cRGD using solid phase synthesis. Peptide disclosed as SEQ ID NO: 758.

The synthetic scheme for cRGD as shown in FIG. 3 is revised based on a reported procedure by Schatzlein et al. *Bioorg. Med. Chem. Lett.* (2002) 12 547-549. NovaSyn TGT alcohol resin (1.25 mmol) (Novabiochem, Calif.) was converted to its active chloride form with acetyl chloride (1 ml/g resin) (62.5 mmol) in toluene for 3 h at 60° C. The resin was then washed with dry toluene and dichloromethane (DCM). The synthesis of linear peptide started with the attachment of aspartic acid, by mixing the chlorinated resin with a solution of Fmoc-Asp-OAll (2.5 eq.) and N, N-diisopropylethylamine (DIPEA) (10 eq.) in dry DCM at rt for 1.5-2.5 h. The solution of DCM, methanol and DIPEA was added to cap the unreacted sites of resin. After 30 min the resin was washed with dimethylformamide (DMF). The Fmoc protecting group was removed with a solution of piperidine-DMF (1:4) at rt for 4 min, 2 times. The rest of amino acids were added consecutively (Fmoc-Gly-OH, Fmoc-Arg(Pbf)-OH, Fmoc-Arg(Pbf)-OH, Fmoc-Lys(Dde)-OH and Fmoc-D-Phe-OH) using standard Fmoc strategy. The amino acid (2 eq.) was added first followed by N,N,N',N'-tetramethyl-O-(7-azabenzotriazol-1-yl)uronium hexafluorophosphate (HATU) (2 eq.) and DIPEA (4 eq.) and allowed to react for 1.5 h at rt. The C-terminal allyl ester group of the aspartic acid was removed after addition of the last amino acid with palladium tetrakis(triphenylphosphine) ($Pd(PPh_3)_4$) (3 eq.) in a solution of chloroform, acetic acid and N-methylmorpholine for 2 h at rt. The mixture was washed with DIPEA in DMF followed by 0.5% w/w diethyldithiocarbamic acid sodium salt in DMF. The head-to-tail cyclization was preformed by removal of the N-terminal Fmoc group before addition of HATU (2 eq.) and DIPEA (4 eq.) in DMF at rt for 16 h. The protecting group of the amino side-chain of lysine (4,4-dimethyl-2,6-dioxocyclohex-1-ylidene)ethyl, (Dde)) was removed by hydrazine monohydrate-DMF (2:98) for 3 min at rt, 3 time. The thiol addition was preformed by swelling resin with DIPEA (15 eq.) in DMF, followed by addition of S-acetylthioglycolic acid N-hydroxysuccinimide ester (SATA) solution (2 eq.) in DMF (15 mg/mL) for 2 h at rt. The resin was then washed with DMF followed by DCM. Next, the protecting group of arginine (pentamethyl-dihydrobenzofuran-5-sulfonyl, (Pbf)) was removed using TFA-DCM (1:1) for 2 h before washing with trifluoroacetic acid-DCM (1:9). The solutions were concentrated and precipitated with cold ether several times. The precipitate was then redissolved in aqueous buffer, purified using reverse phase HPLC and lyophilized to give cRGD peptide (90 mg, 10% yield based on initial loading of resin).

Preparation of cRGD-DOX-Micelles.

20 mg of MAL-PEG-PCL and 2 mg of doxorubicin were dissolved in 0.5 mL THF in a glass vial. Next, the mixture was slowly added into 10 mL of an aqueous solution of 0.05 M HEPES and 0.01 M EDTA under sonication (60 Sonic Dismembrator, Fisher Scientific). The mixture was vigorously stirred under argon for 3 h to remove THF. Then different amounts of c(RGDf(ε-S-acetylthioacetyl)K and 0.05 M hydroxyamine in HEPES/EDTA aqueous solution were added into solutions of micelles with 5, 16, and 76% maleimide density. The conjugation was allowed to occur for 4 h followed by filtration through a Millipore centrifugal filter (pore size 0.45 μm) to remove DOX aggregates in micelle solution. Then the cRGD-micelles were dialyzed with Spectra/Por dialysis membrane (molecular weight cutoff=50,000 Da) until free cRGD was completely removed. Micelles were then characterized by dynamic light scattering and atomic force microscopy. Micelle solutions were then lyophilized to obtain the powdery form. $^1$H NMR was used to confirm the formation of core-shell structure and conjugation of cRGD to micelles. The strong resonance of methylene proton in PEG was detected where as all of caprolactone proton resonance were hardly observed demonstrating the core-shell structure of these micelles. The successful conjugation of cRGD onto the surface of micelles was verified by the appearance of phenyl protons of cRGD at 7.4 ppm.

Atomic Force Microscopy (AFM)

Figure 4:
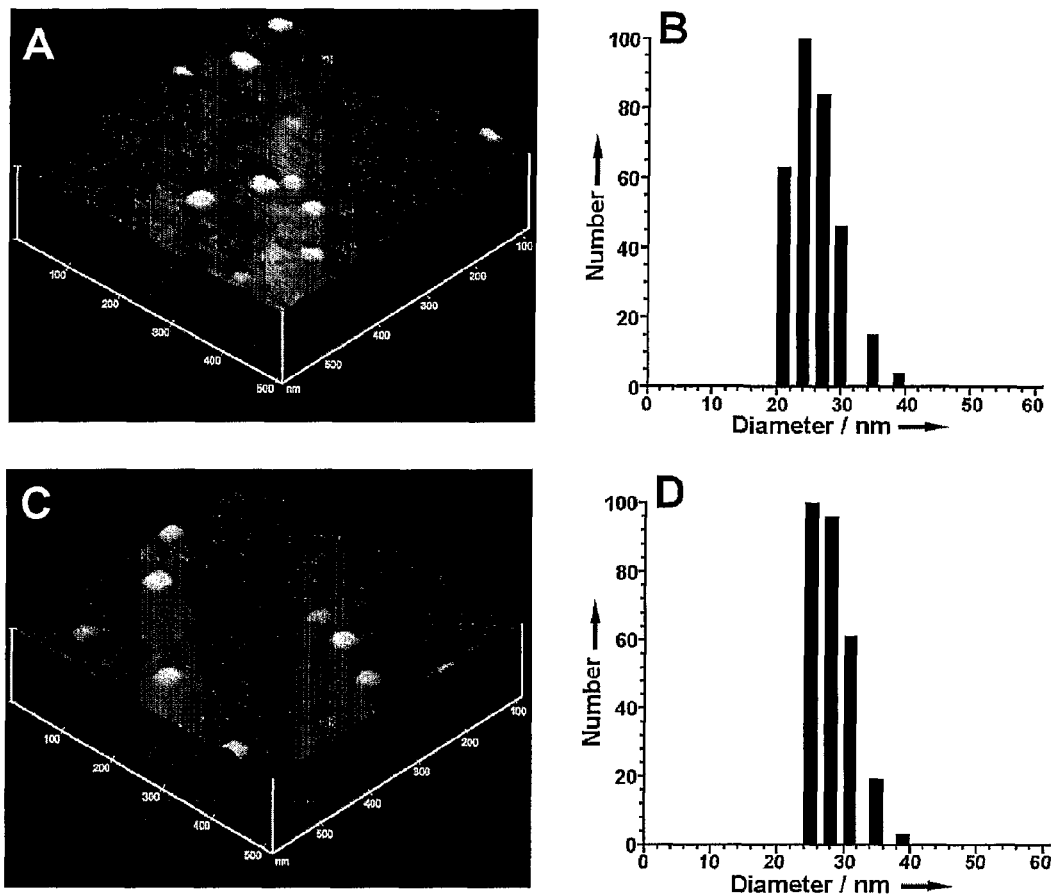
FIG. 4a shows the size characterization of 0% cRGD-DOX micelles by atomic force microscopy.
FIG. 4b shows the size characteristics of 0% cRGD-DOX micelles by dynamic light scattering.
FIG. 4c shows the size characteristics of 76% cRGD-DOX micelles by atomic force microscopy.
FIG. 4d shows the size characteristics of 76% cRGD-DOX micelles by dynamic light scattering.

Two group of micelles were used for AFM study. The first group was DOX-micelles without cRGD ligand and the second group was DOX-micelles with 76% cRGD density. The micelle suspension (2 μL) was placed on the mica surface, and allowed to dry at room temperature overnight before imaging with an atomic force microscope (Multimode, Digital Instruments, Santa Barbara, Calif.) operated in tapping mode using a silicon cantilever (Pointprobe, Nanoworld, Switzerland). The constant force mode was used with a scan frequency of 2 Hz. Both non-functionalized and 76% cRGD containing micelles show discrete and round-shaped nanoparticles. These results were shown in FIGS. 4a and 4c. Micelles with 76% cRGD attachment (43.2±3.9 nm, n=29) showed a mean size slightly larger than that of RGD-free micelles (37.5±2.6 nm, n=29).

Dynamic Light Scattering (DLS)

DLS was performed on a 90 Plus Particle Size Analyzer (Brookhaven Instruments Corporation). Scattered light was detected at 90° at room temperature and collected on an autocorrelator. The data for each sample was obtained in five measurements and the average number was used. The same two groups of micelles as in AFM studies were used for DLS characterization. The sizes of these micelles are 20.9±1.7 and 24.4±2.7 nm for cRGD-free and 76% cRGD micelles, respectively. The results were shown in FIGS. 4b and 4d.

Flow Cytometry Analysis

Figure 6:
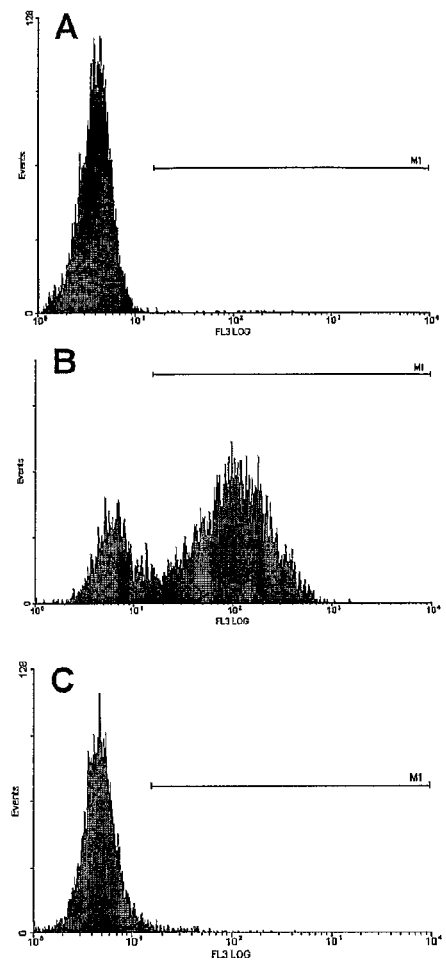
FIG. 6a shows a flow cytometry histogram of micelle uptake in SLK tumor endothelial cells as a function of a cRGD density of 0% on the micelle surface.
FIG. 6b shows a flow cytometry histogram 76% cRGD-micelles in the presence of free RGS ligands (9 mM) in solution.
FIG. 6c shows a flow cytometry histogram of micelle uptake in SLK tumor endothelial cells as a function of a cRGD density of 76% on the micelle surface.

SLK cells were seeded at 125,000 cells/well in 6-well plates in 2 mL DMEM with 10% FBS. After 24 h, 1 mg of micelles (from 3.3 mg/ml micelle suspension) for each micelle formulation with different cRGD density (0, 5, 16, 76% cRGD) was added into each well and incubated at 37° C. for 2 h. Then, cells were washed, trypsinized and neutralized. After centrifugation at 1200 rpm for 5 min, cells were resuspended in 1 mL PBS, followed by filtration and analysis using flow cytometry. Cell uptake was found to increase up to 30-fold with 76% cRGD-DOX-micelles compared to those not attached with cRGD (0% cRGD). In the control experiment, SLK cells were first incubated with a free blocking peptide, Ala-Ala-Arg-Gly-Asp-Tyr (AARGDY) (SEQ ID NO: 757), and then co-incubated with 76% cRGD-functionalized micelles. Almost 100% inhibition by AARGDY (SEQ ID NO: 757) at 9 mM concentration was observed as demonstrated by the flow cytometry histograms as shown in FIG. 6.

Confocal Laser Scanning Microscopy (CLSM)

DOX-micelles with 0 and 16% cRGD density (0.5 mg/well) were incubated with SLK cells (6000 cells/well) culture wells for 2 hrs. Before the CLSM examination, cell nuclei were stained with Hoechst 33342 (Molecular Probes, Inc.). Cells were examined by a Zeiss LSM 510 microscope (Zurich, Switzerland, laser: Ar 351-364 nm, Ar 458-488 nm) with a confocal plane of 300 nm. Doxorubicin and Hoechst 33342 were excited at 485 and 352 nm, respectively. The emission wavelength of doxorubicin and Hoechst 33342 are 595 and 455 nm, respectively. A significantly increased amount of micelle uptake was observed in micelles with 16% cRGD surface density as shown in FIG. 5c compared to those without cRGD as shown in FIG. 5b. This result is consistent with those from flow cytometry studies as shown in FIG. 5a.

Synthesis of DOTA-PEG-PCL

The MPEG-PCL and amino group terminated PEG-PCL polymer ($H_2N$-PEG-PCL) are synthesized following reported procedures (Shuai, X. T. et al., Macromolecules, 2003. 36 5751-5759; Deng, M. X. et al., Biomaterials, (2004) 25 3553-3558). Briefly, synthesis of $H_2N$-PEG-PCL is accomplished by the metalation of acetonitrile with potassium naphthalide to initiate living anionic ring-opening-polymerization with ethylene oxide first and ε-caprolactone (ε-CL) second. Hydrogenation of the CN-PEG-PCL copolymer using Pd/C as catalyst provides a diblock copolymer with a functionalizable amino group ($H_2N$-PEG-PCL). To synthesize the DOTA containing PEG-PCL polymer (DOTA-PEG-PCL), DOTA-NHS ester (Macrocyclics, Inc., Dallas, Tex.) is added to a $H_2N$-PEG-PCL solution in organic solvent. The subsequent copolymer is purified by precipitation in diethyl ether and hexane. Both polymers can be manufactured with various PEG and PCL chain lengths, which can be used to modify both the micelle size and doxorubicin loading within the micelles.

breast tumors. An additional two sets of mice, one with drug-containing, unlabeled micelles and another with drug-free labeled micelles, are injected and imaged as controls.

Additionally, a separate SPECT imaging probe, $^{99m}$Tc-labeled Annexin V can be introduced to simultaneously measure cell apoptosis. One unique property of SPECT imaging is its ability to discern activity from multiple probes that emit gamma photons of different energy, in this case 245 keV for $^{111}$In and 140 keV for $^{99m}$Tc. Prior to use in animals, an in vitro calibration similar to that described above is performed. In this study, vials containing known concentrations of both $^{111}$In-labeled micelles and $^{99m}$Tc-labeled Annexin V are prepared and used to generate limit of detection values for the simultaneous detection of both labels. Animal groups will be the same as those used for $^{111}$In imaging with the addition of a group to receive systemic free doxorubicin to ensure that the tumors in this model are susceptible to doxorubicin treatment. The $^{99m}$Tc-labeled Annexin V is administered via the tail vein prior to each imaging session, and SPECT imaging is used to generate both micelle concentration and apoptosis density Scheme 1

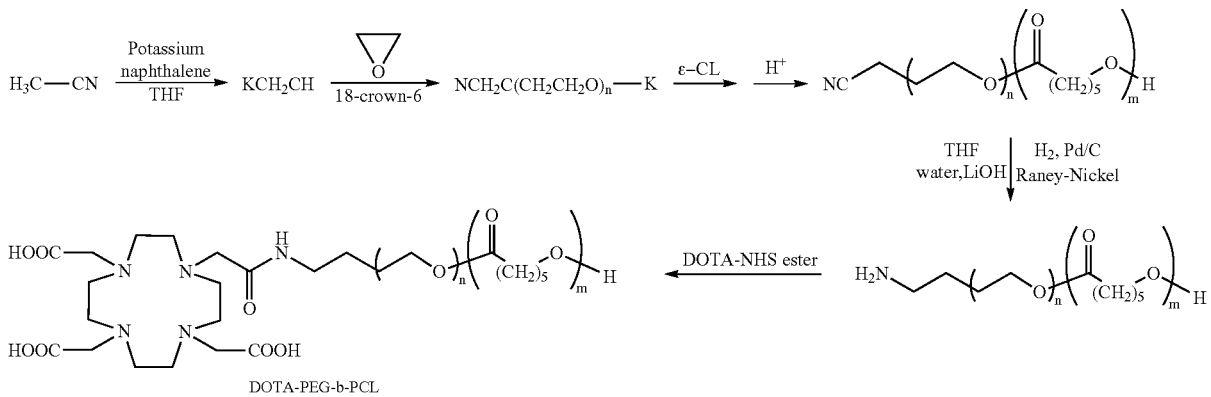

Figure 7:
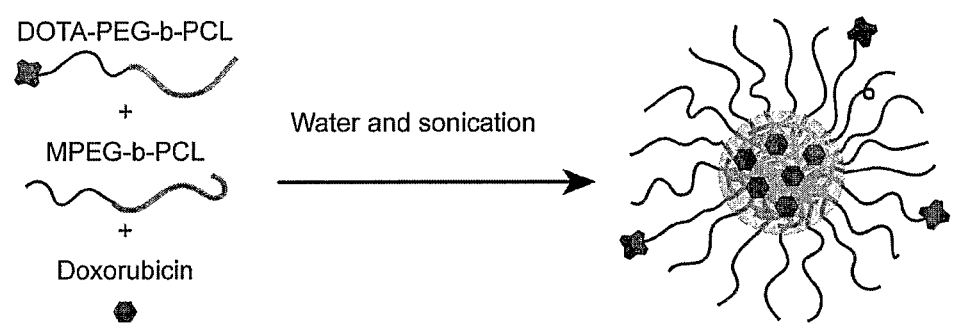
FIG. 7 shows the preparation of DOTA-PEG-b-PCL micelles.

After syntheses of both block copolymers, polymer micelles that incorporate different amounts of chelating agent are fabricated. The amount of chelating agent can be controlled by varying the weight ratio of DOTA-PEG-PCL to MPEG-PCL used. Micelles with 1, 3, and 5% (w/w) DOTA-PEG-PCL are fabricated using a phase inversion technique. A schematic illustrating this process is shown in FIG. 7. Micelle size is characterized through the use of dynamic light scattering and TEM, while drug content and release from the micelles is measured by UV-Vis spectroscopy.

Incorporation of Radioactive Moieties

Immediately prior to each imaging experiment, $^{111}$In is added to each micelle formulation to allow binding of the metal ion to the DOTA chelating group. Excess free $^{111}$In ions are removed through a gel filtration process before imaging, and each micelle sample is serially diluted to generate vials containing a logarithmic range of known concentrations. Multiple vials containing concentrations of each of the three formulations are then imaged via both SPECT and computed tomography (CT), and the resulting imaging activity of each vial is plotted against micelle concentration for that formulation. In this manner, the lower detection limit as well as a calibration value which can be used to convert SPECT activity to micelle concentration is determined for each of the three formulations.

Following in vitro calibration, each of the three micelle formulations are injected into the tail vein of two mice with measurements. The results from this section are confirmed via histological measurements taken after the animals are sacrificed. Tumor volume is measured by gross tissue measurement, doxorubicin concentration in tissue is obtained by fluorescence microscopy, apoptosis is validated using TUNEL stained sections, and micelle concentrations are confirmed by scintillation counting of extracted tissues.

In Vivo Efficacy Data to Optimize the Design of Drug-Loaded Micelles

Different micelle formulations are compared based on their treatment efficacy as measured by total micelle accumulation, apoptotic response, and tumor volume change, all of which are measured non-invasively. Five different micelle formulations are used to investigate the effects of two different micelle properties: size and PEG chain length. These two parameters affect the blood circulations times as well as the extravasation efficiency across the tumor endothelium. Micelle size will be investigated using three micelle formulations with the same PEG length (MW 5 kD) and different PCL lengths (2, 5, and 10 kD). Alternatively, PEG chain length effects are elucidated by using micelle formulations with a fixed PCL length (5 kD) and varying PEG size (2, 5, and 10 kD), for a total of five experimental groups. Control mice are injected with labeled micelles containing no doxorubicin. Each group contains approximately 6 subjects. Once optimized, the micelles are compared directly with systemically administered, dose-matched doxorubicin on the same measures.

Additionally, the data from micelle comparison is used to develop a model to correlate treatment efficacy with micelle accumulation and apoptosis as measured by SPECT. Relationships between micelle accumulation, tumor apoptosis, and tumor volume change over the one week period of monitoring are investigated in order to create a method of predicting the tumor volume change of the tumors based on early (<24 hours) measurements of micelle accumulation and tumor apoptosis.

Micelles Containing SPIO Particles

In FIG. 8a, hydrophobic SPIO particles of approximately 4 nm in diameter were incorporated into the hydrophobic micellar core. In vitro imaging of particle solutions was performed on a Siemens Sonata 1.5T clinical MRI scanner using a fast low angle shoot (FLASH) pulse sequence, and the $T_2$ contrast effect of the micelles was quantified. Particle $T_2$ relaxivity values ranged from 76-102 $(mM\ Fe*s)^{-1}$, suggesting that the particles had largely retained their contrast despite micellar incorporation. For in vivo studies, micelle solutions were injected into the tail vein of breast tumor bearing mice (the bi-transgenic mice bearing both the MMTV-c-neu and LHCTP transgenes proposed for use in this study) at and imaged with $T_2$-weighted sequences at 1 hour and 72 hours after micelle injection. By 72 hours, the peripheral region of the tumor had darkened noticeably, indicating accumulation of SPIO-containing micelles in the region as shown in FIGS. 8b and 8c. MRI has some intrinsic difficulties, however, such as relatively low sensitivity compared to nuclear medicine and problems distinguishing contrast effects from the anatomical background, that promote the development of other imaging modalities for quantitative micelle tracking.

Equivalence

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

The invention claimed is:

1. A micellar structure comprising a biocompatible amphiphilic block copolymer selected from PBLG-PEO, PEO-PPO-PEO, PEG-b-PBLA, and PCL-PEG, a hydrophobic chemotherapeutic agent encapsulated within the micellar structure, a functionalized corona comprising a tissue- or tumor-specific targeting peptide sequence, and an imaging agent comprising an MRI contrast agent encapsulated within the micellar structure, the MRI contrast agent comprising superparamagnetic iron oxide, wherein the tissue-specific targeting peptide sequence and the tumor-specific targeting peptide sequence is selected from SEQ ID Nos 1-756.

2. A micellar structure of claim 1, wherein the amphiphilic copolymer is PCL-PEG.

3. A micellar structure of claim 1, wherein the chemotherapeutic agent is selected from aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

4. A micellar structure of claim 3, wherein the chemotherapeutic agent is selected from paclitaxel and doxorubicin.

5. A micellar structure of claim 1, wherein the peptide sequence is a $\alpha_v\beta_3$ ligand.

6. A micellar structure of claim 5, wherein the $\alpha_v\beta_3$ ligand is cRGD.

7. A micellar structure of claim 1, wherein the functionalized corona comprises a second imaging agent.

8. A micellar structure of claim 7, wherein the second imaging agent comprises a chelating agent.

9. A micellar structure of claim 8, wherein the chelating agent is selected from DOTA, DTPA-BMA, DTPA-BP, and CDTA.

10. A micellar structure of claim 8, further comprising a radioactive moiety that is chelated by the chelating agent.

11. A micellar structure of claim 10, wherein the radioactive moiety is selected from $^{225}$Ac, $^{227}$Ac, $^{241}$Am, $^{198}$Au, $^{7}$Be, $^{212}$Bi, $^{48}$Ca, $^{109}$Cd, $^{139}$Ce, $^{141}$Ce, $^{252}$Cf, $^{55}$Co, $^{57}$Co, $^{60}$Co, $^{51}$Cr, $^{130}$Cs, $^{131}$Cs, $^{137}$Cs, $^{61}$Cu, $^{62}$Cu, $^{165}$Dy, $^{152}$Eu, $^{155}$Eu, $^{18}$F, $^{55}$Fe, $^{59}$Fe, $^{64}$Ga, $^{67}$Ga, $^{68}$Ga, $^{153}$Gd, $^{68}$Ge, $^{111}$In, $^{115m}$In, $^{191m}$Ir, $^{192}$Ir, $^{177}$Lu, $^{51}$Mn, $^{52}$Mn, $^{99}$Mo, $^{95}$Nb, $^{194}$Os, $^{203}$Pb, $^{212}$Pb, $^{103}$Pd, $^{109}$Pd, $^{238}$Pu, $^{223}$Ra, $^{226}$Ra, $^{82}$Rb, $^{186}$Re, $^{188}$Re, $^{105}$Rh, $^{97}$Ru, $^{103}$Ru, $^{145}$Sm, $^{153}$Sm, $^{117m}$Sn, $^{85}$Sr, $^{89}$Sr, $^{90}$Sr, $^{178}$Ta, $^{179}$Ta, $^{182}$Ta, $^{149}$Tb, $^{96}$Tc, $^{99m}$Tc, $^{228}$Th, $^{229}$Th, $^{201}$Tl, $^{170}$Tm, $^{171}$Tm, $^{188}$W, $^{88}$Y, $^{90}$Y, $^{91}$Y, $^{169}$Yb, $^{62}$Zn, $^{65}$Zn, $^{99m}$Tc-labeled Annexin V$^{28}$, and $^{95}$Zr.

12. A micellar structure of claim 11, wherein the radioactive moiety is selected from $^{99m}$Tc-labeled Annexin V$^{28}$, and $^{111}$In.

13. A pharmaceutical composition comprising micelles of claim 1 and a pharmaceutically acceptable carrier.

* * * * *

UNITED STATES PATENT AND TRADEMARK OFFICE
CERTIFICATE OF CORRECTION

PATENT NO. : 8,697,031 B2  
APPLICATION NO. : 11/569989  
DATED : April 15, 2014  
INVENTOR(S) : Ai et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1727 days.

Signed and Sealed this  
Twenty-ninth Day of September, 2015

Michelle K. Lee  
*Director of the United States Patent and Trademark Office*